US010537280B2

(12) United States Patent  
McCrea et al.

(10) Patent No.: US 10,537,280 B2  
(45) Date of Patent: Jan. 21, 2020

(54) DEVICE AND METHOD FOR REMOVAL OF BLOOD-BORNE PATHOGENS, TOXINS AND INFLAMMATORY CYTOKINES

(71) Applicant: EXTHERA MEDICAL CORPORATION, Berkeley, CA (US)

(72) Inventors: Keith McCrea, Concord, CA (US); Robert S. Ward, Orinda, CA (US); George Pitarra, Jr., Berkeley, CA (US)

(73) Assignee: ExThera Medical Corporation, Martinez, CA (US)

( * ) Notice: Subject to any disclaimer, the term of this patent is extended or adjusted under 35 U.S.C. 154(b) by 1160 days.

(21) Appl. No.: 13/966,244

(22) Filed: Aug. 13, 2013

(65) Prior Publication Data

US 2014/0012097 A1    Jan. 9, 2014

Related U.S. Application Data

(63) Continuation of application No. PCT/US2012/025316, filed on Feb. 15, 2012.
(Continued)

(51) Int. Cl.
*A61B 5/00* (2006.01)
*A61B 5/02* (2006.01)
(Continued)

(52) U.S. Cl.
CPC .......... *A61B 5/4836* (2013.01); *A61B 5/0002* (2013.01); *A61B 5/01* (2013.01);
(Continued)

(58) Field of Classification Search
CPC .......... C12M 1/34; C12N 11/08; A61M 1/34; A61M 1/16; A61K 35/14; B82Y 10/00;
(Continued)

(56) References Cited

U.S. PATENT DOCUMENTS 3,782,382 A    1/1974  Naftulin et al.
4,103,685 A    8/1978  Lupien et al.
(Continued)

FOREIGN PATENT DOCUMENTS

CN    101370536 A    2/2009
CN    102740859 A    10/2012
(Continued)

OTHER PUBLICATIONS

International Search Report; PCT/US2015/026340 dated Jul. 28, 2015.
(Continued)

*Primary Examiner* — Michael W Kahelin
*Assistant Examiner* — Vynn V Huh
(74) *Attorney, Agent, or Firm* — Kilpatrick Townsend Stockton LLP

(57) ABSTRACT

The present invention is directed to an integrated system and a method for utilizing the system to detect and remove blood-borne factors of interest, such as pathogens and/or toxins and/or cytokines, from blood or serum (blood) by contacting the blood with a solid, essentially nonporous substrate which has been surface treated with molecules or chemical groups (the adsorbent media or media) having a binding affinity for the pathogens and/or toxins to be removed (the adsorbents). The invention can be used to remove virulence factors, e.g. toxins, that are released from various pathogens. In one aspect, the invention is for the treatment of sepsis and infection, such as infections associated with battle field trauma.

20 Claims, 10 Drawing Sheets

Simplified Schematic of Sepsis DLT System

Related U.S. Application Data

(60) Provisional application No. 61/443,236, filed on Feb. 15, 2011, provisional application No. 61/471,102, filed on Apr. 1, 2011.

(51) Int. Cl.

| | | |
|---|---|---|
| *A61B 5/0205* | (2006.01) | |
| *A61B 5/1468* | (2006.01) | |
| *A61M 1/16* | (2006.01) | |
| *A61B 5/01* | (2006.01) | |
| *A61B 5/145* | (2006.01) | |

(52) U.S. Cl.
CPC ...... *A61B 5/02028* (2013.01); *A61B 5/02055* (2013.01); *A61B 5/1468* (2013.01); *A61B 5/14532* (2013.01); *A61B 5/14542* (2013.01); *A61B 5/14546* (2013.01); *A61B 5/486* (2013.01); *A61M 1/16* (2013.01)

(58) Field of Classification Search
CPC ..... A61B 5/0002; A61B 5/01; A61B 5/02028; A61B 5/02055; A61B 5/0215; A61B 5/145; A61B 5/14532; A61B 5/14542; A61B 5/14546; A61B 5/1468; A61B 5/4836; A61B 5/486; A61B 5/6866
USPC .......................... 435/287.2; 604/500; 600/300
See application file for complete search history.

(56) References Cited

U.S. PATENT DOCUMENTS

| | | |
|---|---|---|
| 4,415,665 A | 11/1983 | Mosbach et al. |
| 4,430,496 A | 2/1984 | Abbott |
| 4,613,665 A | 9/1986 | Larm |
| 4,637,994 A | 1/1987 | Tani et al. |
| 4,820,302 A | 4/1989 | Woodroof |
| 4,955,870 A | 9/1990 | Ridderheim et al. |
| 5,116,962 A | 5/1992 | Stueber et al. |
| 5,211,850 A | 5/1993 | Shettigar et al. |
| 5,403,917 A | 4/1995 | Boos et al. |
| 5,437,861 A | 8/1995 | Okarma et al. |
| 5,447,859 A | 9/1995 | Prussak |
| 5,476,509 A | 12/1995 | Keogh, Jr. et al. |
| 5,753,227 A | 5/1998 | Strahilevitz |
| 6,037,458 A | 3/2000 | Hirai et al. |
| 6,159,377 A | 12/2000 | Davankov et al. |
| 6,197,568 B1 | 3/2001 | Marks et al. |
| 6,248,127 B1 * | 6/2001 | Shah .................... A61L 29/085 427/2.1 |
| 6,312,907 B1 | 11/2001 | Guo et al. |
| 6,461,665 B1 | 10/2002 | Scholander |
| 6,544,727 B1 | 4/2003 | Hei |
| 6,559,290 B1 | 5/2003 | Nakatani et al. |
| 6,653,457 B1 | 11/2003 | Larm et al. |
| 7,179,660 B1 | 2/2007 | Kirakossian |
| 7,408,045 B2 | 8/2008 | Maruyama et al. |
| 7,695,609 B2 * | 4/2010 | Soundarrajan ......... B82Y 10/00 204/403.01 |
| 8,663,148 B2 | 3/2014 | Larm et al. |
| 8,758,286 B2 | 6/2014 | Ward et al. |
| 9,173,989 B2 | 11/2015 | Larm et al. |
| 9,408,962 B2 | 8/2016 | Ward et al. |
| 9,669,150 B2 | 6/2017 | Larm et al. |
| 9,764,077 B2 | 9/2017 | Larm et al. |
| 10,086,126 B2 | 10/2018 | Ward et al. |
| 10,188,783 B2 | 1/2019 | Larm et al. |
| 2001/0005487 A1 * | 6/2001 | Kamibayashi ......... A61M 1/16 422/45 |
| 2002/0018985 A1 | 2/2002 | Eibl et al. |
| 2002/0058032 A1 | 5/2002 | Hirai et al. |
| 2002/0068183 A1 | 6/2002 | Huang et al. |
| 2002/0197249 A1 | 12/2002 | Brady et al. |
| 2002/0197252 A1 | 12/2002 | Brady et al. |
| 2003/0021780 A1 | 1/2003 | Smith et al. |
| 2003/0044769 A1 | 3/2003 | Ogino et al. |
| 2003/0148017 A1 | 8/2003 | Tuominen et al. |
| 2004/0084358 A1 | 5/2004 | O'Mahony et al. |
| 2004/0115278 A1 | 6/2004 | Putz et al. |
| 2004/0140265 A1 | 7/2004 | Lihme |
| 2004/0176672 A1 * | 9/2004 | Silver ................... A61B 5/0031 600/345 |
| 2004/0182783 A1 * | 9/2004 | Walker .................. A61L 2/0011 210/639 |
| 2004/0185553 A9 | 9/2004 | Hei |
| 2004/0202783 A1 | 10/2004 | Baumann et al. |
| 2005/0098500 A1 | 5/2005 | Collins et al. |
| 2005/0142542 A1 | 6/2005 | Hei et al. |
| 2005/0244371 A1 | 11/2005 | Lentz |
| 2005/0271653 A1 * | 12/2005 | Strahilevitz ............. C07K 1/22 424/140.1 |
| 2006/0093999 A1 | 5/2006 | Hei |
| 2006/0252054 A1 | 11/2006 | Ping |
| 2007/0190050 A1 | 8/2007 | Davidner et al. |
| 2007/0218514 A1 | 9/2007 | Smith et al. |
| 2007/0231217 A1 | 10/2007 | Clinton et al. |
| 2008/0021365 A1 | 1/2008 | Kobayashi et al. |
| 2008/0138434 A1 * | 6/2008 | Brady ................. A61M 1/3679 424/529 |
| 2008/0268464 A1 | 10/2008 | Schumacher et al. |
| 2008/0314817 A1 | 12/2008 | Fujita et al. |
| 2009/0105194 A1 | 4/2009 | Flengsrud et al. |
| 2009/0136586 A1 | 5/2009 | Larm et al. |
| 2009/0173685 A1 | 7/2009 | Imai et al. |
| 2009/0206038 A1 | 8/2009 | Thomas |
| 2009/0246800 A1 | 10/2009 | Mattingly et al. |
| 2009/0325276 A1 | 12/2009 | Battrell et al. |
| 2010/0069816 A1 | 3/2010 | Brady et al. |
| 2010/0079360 A1 * | 4/2010 | McLaughlin ........ A61B 5/7445 345/76 |
| 2010/0098666 A1 | 4/2010 | Wright |
| 2010/0112725 A1 | 5/2010 | Babu et al. |
| 2010/0145317 A1 * | 6/2010 | Laster .................. A61B 5/0031 604/891.1 |
| 2010/0216226 A1 | 8/2010 | Hyde et al. |
| 2010/0217173 A1 | 8/2010 | Hyde et al. |
| 2010/0239673 A1 | 9/2010 | Linhardt et al. |
| 2010/0249689 A1 | 9/2010 | Larm et al. |
| 2010/0276359 A1 | 11/2010 | Ippommatsu et al. |
| 2010/0291588 A1 * | 11/2010 | McDevitt .......... B01L 3/502715 435/7.2 |
| 2010/0326916 A1 * | 12/2010 | Wrazel .................... A61M 1/16 210/646 |
| 2011/0150911 A1 | 6/2011 | Choo et al. |
| 2011/0171713 A1 | 7/2011 | Bluchel et al. |
| 2011/0184377 A1 | 7/2011 | Ward et al. |
| 2011/0224645 A1 | 9/2011 | Winqvist et al. |
| 2012/0040429 A1 | 2/2012 | Federspiel et al. |
| 2012/0305482 A1 | 12/2012 | McCrea et al. |
| 2013/0102948 A1 | 4/2013 | Reich et al. |
| 2013/0131423 A1 | 5/2013 | Wang et al. |
| 2014/0131276 A1 | 5/2014 | Larm et al. |
| 2014/0231357 A1 | 8/2014 | Ward et al. |
| 2015/0111849 A1 | 4/2015 | McCrea et al. |
| 2015/0260715 A1 | 9/2015 | Hu et al. |
| 2016/0022898 A1 | 1/2016 | Larm et al. |
| 2016/0082177 A1 | 3/2016 | Ward et al. |
| 2016/0084835 A1 | 3/2016 | Ward et al. |
| 2016/0101229 A1 | 4/2016 | McCrea et al. |
| 2016/0214935 A1 | 7/2016 | Hutchinson et al. |
| 2016/0331886 A1 | 11/2016 | Ward et al. |
| 2017/0035956 A1 | 2/2017 | McCrea et al. |
| 2017/0073727 A1 | 3/2017 | Ward et al. |
| 2017/0340803 A1 | 11/2017 | Larm et al. |
| 2018/0361050 A1 | 12/2018 | Ward et al. |
| 2019/0038826 A1 | 2/2019 | McCrea et al. |
| 2019/0143027 A1 | 5/2019 | Larm et al. |

FOREIGN PATENT DOCUMENTS

| | | |
|---|---|---|
| DE | 4217917 A1 | 12/1993 |
| EP | 0 306 617 A | 3/1989 |

(56) References Cited

FOREIGN PATENT DOCUMENTS

| | | |
|---|---|---|
| EP | 0 321 703 A | 6/1989 |
| EP | 0533946 A1 | 3/1993 |
| EP | 0 616 845 A | 9/1994 |
| EP | 0 810 027 A | 12/1997 |
| EP | 1044696 A2 | 10/2000 |
| EP | 1 057 529 A | 12/2000 |
| EP | 1 110 602 A | 6/2001 |
| EP | 1 219 639 A | 7/2002 |
| EP | 2087916 A1 | 8/2009 |
| EP | 2556849 A1 | 2/2013 |
| GB | 2 172 812 A | 10/1986 |
| JP | 58-053757 A | 3/1983 |
| JP | 4-89500 A | 3/1992 |
| JP | 6040926 A | 2/1994 |
| JP | 6-505248 A | 6/1994 |
| JP | 7-178161 A | 7/1995 |
| JP | 96-510166 A | 10/1996 |
| JP | 11-502703 A | 3/1999 |
| JP | 2000-086688 A | 3/2000 |
| JP | 200-217575 A | 8/2000 |
| JP | 2000-515543 A | 11/2000 |
| JP | 2002-505101 A | 2/2002 |
| JP | 2003-128502 A | 5/2003 |
| JP | 2005-514127 A | 5/2005 |
| JP | 2005-532130 A | 10/2005 |
| JP | 2009-521413 A | 6/2009 |
| KR | 10-2008-0077405 A | 8/2008 |
| WO | 91/04086 A | 4/1991 |
| WO | 92/14361 A1 | 9/1992 |
| WO | 94/26399 A1 | 11/1994 |
| WO | 95/05400 | 2/1995 |
| WO | 96/29083 A1 | 9/1996 |
| WO | 96/40857 A1 | 12/1996 |
| WO | 97/35660 A1 | 10/1997 |
| WO | 98/05341 A1 | 2/1998 |
| WO | 98/29727 A2 | 7/1998 |
| WO | 99/06086 A1 | 2/1999 |
| WO | 99/45104 A3 | 11/1999 |
| WO | 00/23792 | 4/2000 |
| WO | 00/038763 | 7/2000 |
| WO | 00/66260 A | 11/2000 |
| WO | 01/18060 A | 3/2001 |
| WO | 02/060512 | 8/2002 |
| WO | 03/033143 A1 | 4/2003 |
| WO | 2003/057356 A2 | 7/2003 |
| WO | 2004/008138 A2 | 1/2004 |
| WO | 2004/009798 A2 | 1/2004 |
| WO | 2005/021799 A2 | 3/2005 |
| WO | 2007/058592 A1 | 5/2007 |
| WO | 2007/069983 A1 | 6/2007 |
| WO | 2007/101064 A2 | 9/2007 |
| WO | 2007/146162 A2 | 12/2007 |
| WO | 2008/095905 A2 | 8/2008 |
| WO | 2008/157570 A2 | 12/2008 |
| WO | 2010/029317 A2 | 3/2010 |
| WO | 2011/068897 A1 | 6/2011 |
| WO | 2011/100354 A1 | 8/2011 |
| WO | 2012/112724 A1 | 8/2012 |
| WO | 2012/172341 A2 | 12/2012 |
| WO | 2013/188073 A1 | 12/2013 |
| WO | 2014/209782 A1 | 12/2014 |
| WO | 2015/069942 A1 | 5/2015 |
| WO | 2015/164198 A1 | 10/2015 |

OTHER PUBLICATIONS

International Search Report; PCT/US2015/051239 dated Dec. 17, 2015.
Popova et al., "Acceleration of epithelial cell syndecan-1 shedding by anthrax hemolytic virulence factors," BMC Microbiolgoy, 2006, vol. 6:8, pp. 1-16.
Bindslev et al., Treatment of acute respiratory failure by extracorporeal carbon dioxide elimination performed with a surface heparinized artificial lung,• Anesthesiology, 1987, vol. 67, pp. 117-120.
Chen et al., *Mol. Cells*, vol. 26, pp. 415-426, 2008.
Dixon et al., "Anthrax," New England Journal of Medicine, Sep. 1999, vol. 341(11), pp. 815-826.
Haase et al., "The effect of three different miniaturized blood purification devices on plasma cytokine concentration in an ex vivo model of endotoxinemia," Int. J. Artif. Organs, 2008, vol. 31, pp. 722-729.
Keuren et al., "Thrombogenecity of polysaccharide-coated surfaces," 2003, *Biomaterials*, vol. 24, pp. 1917-1924.
Larm et al., "A new non-thrombogenic surface prepared by selective covalent binding of heparin via a modified reducing terminal residue," Biomater Med Devices Artif Organs, 1983, vol. 11, pp. 161-173.
Mandal, "Sialic acid binding Lectins," Experientia, 1990, vol. 46, pp. 433-439.
Mariano et al, "Tailoring high-cut-off membranes and feasible application in sepsis-associated acute renal failure: in vitro studies," *Nephrol Dial Transplant*, 2005, vol. 20, pp. 1116-1126.
Ofek et al., "Mannose Binding and Epithelial Cell Adherence of *Escherichia coli*," Infection and Immunity, 1978, vol. 22, pp. 247-254.
Riesenfeld et al., "Quantitative analysis of N-sulfated, N-acetylated, and unsubstituted glucosamine amino groups in heparin and related polysaccharides," Anal Biochem, 1990, vol. 188, pp. 383-389.
Sagnella et al., "Chitosan based surfactant polymers designed to improve blood compatibility on biomaterials," *Colloids and Surfaces 8: Biointerfaces*, 2005, vol. 42, pp. 147-155.
Schefold et al., "A novel selective extracorporeal intervention in sepsis: immunoadsorption of endotoxin, interleukin 6, and complement-activating product 5a," Shock, 2007, vol. 28, pp. 418-425.
Sharon, "Bacterial lectins, cell-cell recognition and infectious disease," FEBS letters, 1987, vol. 217, pp. 145-157.
Swartz, "Recognition and management of anthrax: an update," New England Journal of Medicine, Nov. 2001, vol. 345(22), pp. 1621-1626.
Thomas et al., "Common ollgosaccharide moieties inhibit the adherence of typical and atypical respiratory pathogens," Journal of Microbiology, Sep. 2004, vol. 53, No. Pt. 9, pp. 833-840.
Weber et al., "Development of specific adsorbents for human tumor necrosis factor-alpha: influence of antibody immobilization on performance and biocompatibility," Biomacromolecules, 2005, vol. 6, pp. 1864-1870.
Wendel et al., *European Journal of Cardio•thoracic Surgery*, 1999, vol. 16, pp. 342-350.
Bjorklund et al., Abstract of "Synthesis of silica-based heparin-affinity adsorbents," J. Chrom. A., 728(1-2):149-169, 1996.
Dubreuil et al., "Effect of heparin binding on Helicobacter pylori resistance to serum," J. Med. Micro., 53:9-12, 2004.
Fujita, M. et al., "Adsorption of inflammatory cytokines using a heparin-coated extracorporeal circuit," Artificial Organs, 26(12):1020-1025, 2002.
Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectins12/Hirmo/paper.htm>.
International Search Report; PCT/US2012/025316 dated May 23, 2012.
International Search Report; PCT/US2010/058596 dated Mar. 29, 2011.
International Search Report; PCT/US2011/024229 dated May 30, 2011.
International Search Report; PCT/SE2006/001421 dated Mar. 30, 2007.
International Search Report; PCT/US2013/042377 dated Sep. 9, 2013.
International Search Report; PCT/US2014/043358 dated Dec. 1, 2014.
International Search Report; PCT/US2014/064419 dated Feb. 12, 2015.
Kim et al., "Role of the heparin in regulating a transcapillary exchange in far north conditions," Bulletin of the Siberian Branch of the Russian Academy of Medical Sciences, 2(108), 2003.

(56) References Cited

OTHER PUBLICATIONS

Lopatkin et al., "Efferent methods in medicine, M.," Medicine, pp. 266, 272-273, 276-279, 1989.
Nadkarni et al., Abstract of "Directional immobilization of heparin onto beaded supports," Anal. Biochem., 222(1):59-67, 1994.
Park, P. et al., "Activation of Syndecan-1 ectodomain shedding by Staphylococcus aureus α-toxin and β-toxin," J. Biol. Chem., 279(1):251-258, 2004.
Sanchez, J. et al., "Control of contact activation on end-point immobilized heparin: The role of antithrombin and the specific antithrombin-binding sequence," J. Bio. Mat. Res., 29:665-661, 1995.
Sasaki et al., Abstract of "Improved method for the immobilization of heparin," J. Chrom., 400:123-32, 1987.
Ward et al., "Specificity of adsorption in a prototype whole blood affinity therapy device for removal of Staphylococcus aureus," Society for Biomaterials 2013 Annual Meeting and Exposition, Apr. 10, 2013, p. 1.
Weir, D., "Carbohydrates as recognition molecules in infection and immunity," FEMS Microbiology Immunology, 47:331-340, 1989.
Yu, J. et al., "Adhesion of coagulase-negative staphylococci and adsorption of plasma proteins to heparinized polymer surfaces," Biomaterials, 15(10):805-814, 1994.
Zhou et al., Abstract of "Heparin-agarose aqueous ethanol suspension," J. Mol. Bio., 271(3):12, 1997.
International Search Report for PCT/US2012/025316 dated May 23, 2012.
International Preliminary Report on Patentability, dated Aug. 21, 2013, PCT application No. PCT/ISA/237; 8 pages.
Utt, M. et al., "Identification of heparan sulphate binding surface proteins of Helicobacter pylori: inhibition of heparan sulphate binding with sulphated carbohydrate polymers," J. Med. Microbiol., 46:541-546, 1997.
Francy, D. et al., "Comparison of filters for concentrating microbial indicators and pathogens in lake water samples," Applied and Environmental Microbiology, 79(4):1342-52, 2012.
Millen, H. et al., "Glass wool filters for concentrating waterborne viruses and agricultural zoonotic pathogens," J. Vis. Exp., 61:e3930, 2012.
Bhakdi, S. and Tranum-Jensen, J., "Alpha-toxin of Staphylococcus aureus," Microbiological Reviews, 55(4):733-751, 1991.
International Search Report; PCT/US2016/057121 dated Dec. 30, 2016.
Abdul-Razzak, K. et al., "Fetal and newborn calf thymus as a source of chromatin proteins: Purification of HMG-1 and HMG-2," Preparative Biochemistry and Biotechnology, 17(1):51-61, 1987.
Alarabi, A. et al., "Treatment of pruritus in cholestatic jaundice by bilirubin- and bile acid-adsorbing resin column plasma perfusion," Scandinavian Journal of Gastroenterology, 27(3):223-6, 1992.
Chase, H., "Affinity separations utilising immobilised monoclonal antibodies—a new tool for the biochemical engineer," Chemical Engineering Science, 39(7-8)1099-1125, 1984.
Garg, L. et al., "Isolation and separation of HMG proteins and histones H1 and H5 and core histones by column chromatography on phosphocellulose," Protein Expression and Purification, 14(2):155-159, 1998.

Low, R. et al., "Protein n, a primosomal DNA replication protein of Escherichia coli," Journal of Biological Chemistry, 257(11):6242-6250, 1982.
Rauvala, H. et al., "Isolation and some characteristics of an adhesive factor of brain that enhances neurite outgrowth in central neurons," Journal of Biological Chemistry, 262(34):16625-16635, 1987.
Rauvala, H. et al., "The adhesive and neurite-promoting molecule p30: Analysis of the amino-terminal sequence and production of antipeptide antibodies that detect p30 at the surface of neuroblastoma cells and of brain neurons," Journal of Cell Biology, 107(6,1):2293-2305, 1988.
Salmivirta, M. et al., "Neurite growth-promoting protein (Amphoterin, p30) binds syndecan," Experimental Cell Research, 200:444-451, 1992.
Sato, T. et al., "Experimental study of extracorporeal perfusion for septic shock," Asaio Journal, 39(3):M790-M793, 1993.
Wang, H. et al., "HMG-1 as a late mediator of endotoxin lethality in mice," Science, 285:248-251, 1999.
Axelsson, J. et al., "Cytokines in blood from septic patients interact with surface-immobilized heparin," ASAIO Journal, 56:48-51, 2010.
Celik, T. et al., "Treatment of lyme neuroborreliosis with plasmapheresis," J. Clinical Apheresis, 31:476-478, 2016.
International Search Report; PCT/US2017/058536; dated Jan. 17, 2018.
Kenig, M. et al., "Identification of the heparin-binding domain of TNF-alpha and its use for efficient TNF-alpha purification by heparin-Sepharose affinity chromatography," J. Chromatography B, 867:119-125, 2008.
Kishimoto, S. et al., "Human stem cell factor (SCF) is a heparin-binding cytokine," J. Biochem., 145(3):275-278, 2009.
Salek-Ardakani, S. et al., "Heparin and heparan sulfate bind interleukin-10 and modulate its activity," Blood, 96:1879-1888, 2000.
Alfaro et al., "Interleukin-8 in cancer pathogenesis, treatment and follow-up," Cancer Treat Rev., Nov. 2017, vol. 60:24-31 (abstract only).
Kumari, N. et al., "Role of interleukin-6 in cancer progression and therapeutic resistance," Tumour Biol., Sep. 2016, vol. 37(9), pp. 11553-11572 (abstract only).
Lian, S. et al., "Elevated expression of growth-regulated oncogene-alpha in tumor and stromal cells predicts unfavorable prognosis in pancreatic cancer," Medicine, Jul. 2016, 95(30), pp. 1-8.
Mattsby-Baltzer, I. et al., "Affinity apheresis for treatment of bacteremia caused by Staphylococcus aureus and/or methicillin-resistant S. aureus (MRSA)," J. Microbiol. Biotechnol., 21(6):659-664, 2011.
Waugh D. and Wilson, C., "The interleukin-8 pathway in cancer," Clin. Cancer Res., 14(21):6735-41, 2008.
Webb, L. et al., "Binding to heparan sulfate or heparin enhances neutrophil responses to interleukin 8," PNAS USA, 90:7158-62, 1993.
GE Healthcare, "Size exclusion chromatography columns and resins, Selection guide," 2010, retreived online at <<https://cdn.gelifesciences.com/dmm3bwsv3/AssetStream.aspx?mediaformatid=10061&destinationid=10016&assetid=13947>> on Jun. 27, 2019, 10 pages.

* cited by examiner

Simplified Schematic of Sepsis DLT System

QCM plot. Mass of heparin absorbed

Fast Clearance

**Removal of *B. anthracis* protective antigen (PA) toxin from serum**

FIG. 6

| Bacteria | Viruses | Toxins | Parasites |
|---|---|---|---|
| *Bacillus Anthracis* | HIV | *B. Anthracis* Protective Antigen (PA) | *Plasmodium falciparum* |
| *Staphylococcus aureus and MRSA* | Hepatitis C | MRSA alpha toxin | |
| *Pseudomonus aeruginosa* | Dengue Virus | | |

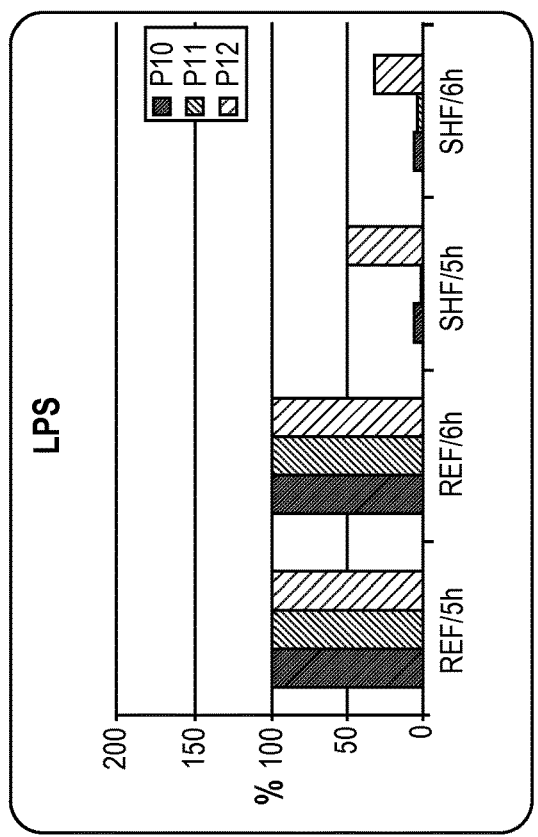
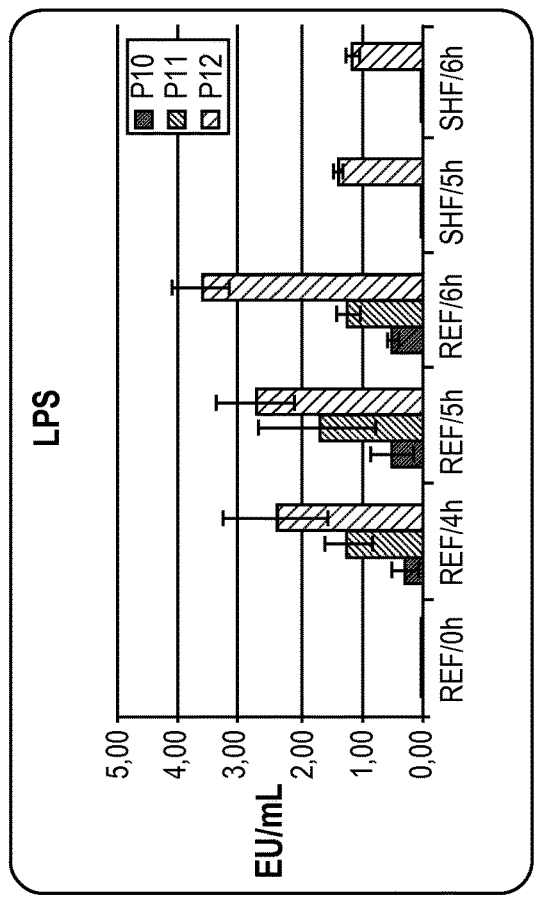
FIG. 10

DEVICE AND METHOD FOR REMOVAL OF BLOOD-BORNE PATHOGENS, TOXINS AND INFLAMMATORY CYTOKINES

CROSS-REFERENCE TO RELATED APPLICATIONS

This application is a continuation of PCT/US2012/025316, filed Feb. 15, 2012, which claims priority to U.S. Provisional Application No. 61/443,236, filed Feb. 15, 2011, and U.S. Provisional Application No. 61/471,102, filed Apr. 1, 2011, the disclosures of which are hereby incorporated by reference in their entirety for all purposes.

FIELD OF THE INVENTION

The present invention is directed to an integrated system and a method for utilizing the system to detect and remove blood-borne factors of interest, such as pathogens and/or toxins and/or cytokines, from blood or serum (blood) by contacting the blood with a solid, essentially nonporous substrate which has been surface treated with molecules or chemical groups (the adsorbent media or media) having a binding affinity for the pathogens and/or toxins to be removed (the adsorbents). The invention can be used to remove virulence factors, e.g. toxins, that are released from various pathogens. In one aspect, the invention is for the treatment of sepsis and infection, such as infections associated with battle field trauma.

The present invention also provides a method of treating a disease (such as sepsis) by removing pathogens and/or toxins from blood by contacting blood with an essentially nonporous substrate coated with heparin and/or other adsorbent materials, and a system for performing the method and treatment.

BACKGROUND

Heparin is an anticoagulant, anti-inflammatory and bacteriostatic polysaccharide, that can be isolated from mammalian tissue, synthetically modified or purified, and/or synthesized artificially. It has a very specific distribution in mammalian tissue; being present only in the basophilic granules of mast cells. Since its discovery in 1916 by the American scientist McLean, heparin has been recognized for its ability to prevent blood from clotting, and for its relatively short half-life in the body. Systemic heparin, administered by injection of the free drug, has been used clinically for more than 50 years as a safe and effective blood anticoagulant and antithrombotic agent. The effects of heparin on blood coagulation/clotting diminish fairly quickly after administration is halted, making its use during surgery and other procedures effective and safe. That is, heparin's anticoagulant and antithrombogenic properties are useful during many medical procedures, for example to minimize undesirable interactions between blood and the man-made surfaces of extracorporeal circuits. Once the procedure is over, the administration of heparin may be then terminated. The heparin concentration in the patient's blood diminishes to a safe level within a few hours. This is particularly important following surgery when healing depends on the ability of blood to clot at the surgical site to avoid bleeding complications. In addition to its well established and continuing use in the treatment of thromboembolic disorders and the prevention of surface-induced thrombogenesis, heparin has more recently been found to have a wide range of other functions apparently unrelated to its function as an anticoagulant. For example, a large number of proteins in blood are now known to bind with high affinity, to free/soluble heparin and/or the closely-related polysaccharide heparan sulfate which is also found in animal tissue, including the luminal surface of healthy blood vessels. Examples are antithrombin (AT), fibronectin, vitronectin, growth factors (e.g. the fibroblast growth factors, the insulin like growth factors, etc.). Human serum albumin (HSA) also binds, but with a lower affinity despite its high concentration in blood.

Infection remains a leading cause of death for battle trauma patients. Due to the nature of the wounds suffered by wounded warriors, 35% of battle trauma patients acquire infections, as opposed to a 9-13% infection rate in civilian trauma patients. Infected patients are at risk of sepsis, in which the patient's immune system over reacts and a "cytokine storm" occurs, where cytokines are released from inflammatory cells in toxic concentrations. The body's own defense system begins to attack healthy tissue, often leading to multiple organ failure and death. Although antibiotics are generally effective in treating an infection, there are very few treatments that attempt to reduce the inflammation caused during sepsis.

Outside the military, more than 750,000 people in the United States develop severe sepsis every year, a syndrome characterized by an overwhelming systemic response to infection that can rapidly lead to organ failure and ultimately death. Additionally, sepsis may elicit the onset of both abnormal clotting and bleeding leading to disseminated intra-vascular coagulation (DIC). Thirty percent of people with sepsis die from its consequences within the first month; up to 50 percent die within six months. The individuals who are most vulnerable to sepsis are wounded warriors, neonates, children, the elderly, and people whose immune systems are compromised by medical treatment, e.g., for cancer, organ transplantation or immune-suppressing diseases such as AIDS.

After many attempts at a pharmacological treatment, survival rates remained unimproved. New clinical protocols, from the Surviving Sepsis Campaign, have made impressive improvements, largely through prevention, but totally new therapies for infected patients are still needed. A serious limitation is the time required to perform cell cultures for pathogen identification for proper antibiotic selection. However, widespread use of antibiotics has itself created resistant strains, suggesting that a biomimetic device-based therapy may be more effective overall.

Drug-resistant bacterial strains are also a major concern for the military. In a recent study, it was found that 70% of *S. aureus* (SA) infections of service members deployed in Iraq are identified as Methicillin-Resistant *S. aureus* (MRSA). As broad-spectrum antibiotics are used more frequently, it is expected that new drug-resistant strains will continue to evolve.

The Dual Challenges of Clotting and Intrinsic Separation from a Complex Fluid

When any conventional foreign material is placed in contact with blood, the intrinsic pathway (contact phase) of the coagulation cascade is initiated. Within the first 200 seconds of contact, protein adsorption occurs on the foreign surface and many reactions between enzymes and proteins take place. The culmination of the coagulation cascade is the cleaving of fibrinogen to produce a fibrin clot responsible for thrombus formation and can ultimately leave to form a circulating blood clot or embolus. Emboli can clog blood vessels, depriving downstream tissue of blood, with often life-threatening consequences. A parallel process is platelet adsorption and activation, also by thrombin, in which the platelets change shape and form platelet aggregates. The interaction of blood and a medical device is complicated further by the simultaneous initiation of the extrinsic pathway of the coagulation cascade when tissue factor is exposed. To counteract both pathways of the coagulation cascade during medical procedures, anticoagulants are administered to decrease the rate of fibrin formation by accelerating the rate of Thrombin deactivation. Unfortunately, uncontrolled bleeding and spontaneous hemorrhage can occur with such procedures and is clearly a risk for wounded warriors. Longer term use of soluble systemic heparin can lead to heparin-induced thrombocytopenia, a chronic condition involving severe platelet depletion. Virtually all, materials used in conventional dialysis, and high-surface-area, nano-porous media separation technologies suffer from clotting risks.

Several dialysis-like therapy (DLT) separation technologies for sepsis treatment have been tested by others with little success. They used either dialysis membranes or high-surface area nano-porous supports similar to chromatography media to capture inflammatory molecules, but not bacteria or other adsorbates too large to enter the nano-scale pores of the adsorption media. Continuous veno-venous hemofiltration and high-volume hemofiltration have shown positive results for septic patients with renal failure, but conclusive evidence for benefit of patients without renal failure is lacking.

Additionally, deleterious effects may occur with these earlier technologies. The disadvantage of current technologies include 1) reliance on slow diffusion kinetics within the media's nano-sized pores 2) indiscriminate capture, 3) lack of pathogen capture, 4) use of artificial materials that ironically increase inflammation and 5) need for systemic anticoagulation. In addition, so-called size exclusion separation is difficult in clinical practice since many of the biomarkers (e.g. kidney-creatinine and liver-bilirubin) used by clinicians to evaluate patient status are removed by the separation process itself. One technology that is showing promise in treating Gram negative sepsis uses surface immobilized polymyxin B to capture endotoxins from blood. However, polymyxin B is cationic and is inherently very thrombogenic. In order to prevent coagulation and emoboli formation systemic anticoagulation is required with its attendant complications.

BRIEF DESCRIPTION OF THE DRAWINGS

FIG. 6—Adsorption Removal of *B. anthracis* protective antigen (PA) toxin from serum. Two different strains of *B. anthracis* were cultured. Strain 7702 produces PA while strain 9131 does not. A supernatant from strain 7702 was passed over the heparinized media and PA was reduced to background levels.

FIG. 7—Removal of MRSA alpha toxin. A supernatant containing alpha toxin was passed over the heparinized media and the toxin was reduced to background levels.

FIG. 8—Blood—borne factors of interest known to bind to heparan sulfate

FIG. 9—Pressure vs. flow rate of saline flowing through a hemofilter.

FIG. 10—Removal of endotoxin from LPS incubated human blood. Incubated blood was re-circulated through a cartridge containing and inlet and outlet layer of heparinized beads surrounding a mixture of heparinized and aminated beads.

SUMMARY OF THE INVENTION

The present invention avoids the pitfalls of the previously available therapies by providing 1) rapid adsorption kinetics based on convection transport of adsorbates to binding sites on the surface of the adsorption media, 2) specific capture of desired target molecules, 4) a safe, natural anticoagulant which minimizes inflammation, and 5) operation without the need for systemic anticoagulation. Operation without systemic anticoagulants is particularly important for treating wounded warriors, or other trauma victims with life-threatening bleeding from their wounds and/or surgery.

The ideal surface for blood-contacting biomedical devices is one that mimics the healthy endothelium of a blood vessel, which naturally prevents surface-induced thrombosis. In addition to preventing thrombosis, an artificial surface that mimics an endothelial cell wall can become a target for pathogens, toxins, and inflammatory molecules (hereinafter "blood-borne factors of interest").

An important aspect of the present invention's intrinsic separation technology is its ability to present a safe, anti-thrombogenic surface that also mimics the endothelial cell wall. A foundation of the present technology is covalently-bound end-point attached heparin that not-only provides an antithrombogenic surface, but also provides a mechanism of action to remove many pathogens.

An object of the present invention is to provide a method and device for the removal of pathogens, or toxins from pathogens from mammalian blood by contacting that blood with a solid, essentially nonporous substrate with a surface layer of heparin, heparan sulphate, and/or other selective adsorbent molecules, biomolecules or chemical groups.

The present invention includes a dialysis-like therapy (DLT) Device. The feasibility of a broad-spectrum whole-blood separation technology that uses covalently-bonded heparin on a high-surface-area polymer substrate in a disposable cartridge is herein established. The present system and methods create a biomimetic diversion for harmful substances in blood (i.e., the "blood-borne factors of interest"), which bind to the surface of the present novel extracorporeal cartridge instead of onto heparan sulfate segments on endothelial cells.

In the present methods, systems and devices, pathogenic microbes often bind without releasing cellular contents, reducing the patient's pathogen load. In one embodiment, the present system and methods apply a single, broad-spectrum, anti-thrombogenic cartridge, a novel biosensor, a roller, or rotary or pulsatile blood pump, and 'smart' patient monitor in a compact unit. (See, for example FIG. 1). Non-leaching heparin on all blood-contacting surfaces and laminar flow through micro-channels larger than blood cells in the cartridge eliminate the need for systemic anticoagulation and the associated risks of bleeding and heparin-induced thrombocytopenia.

Figure 1:
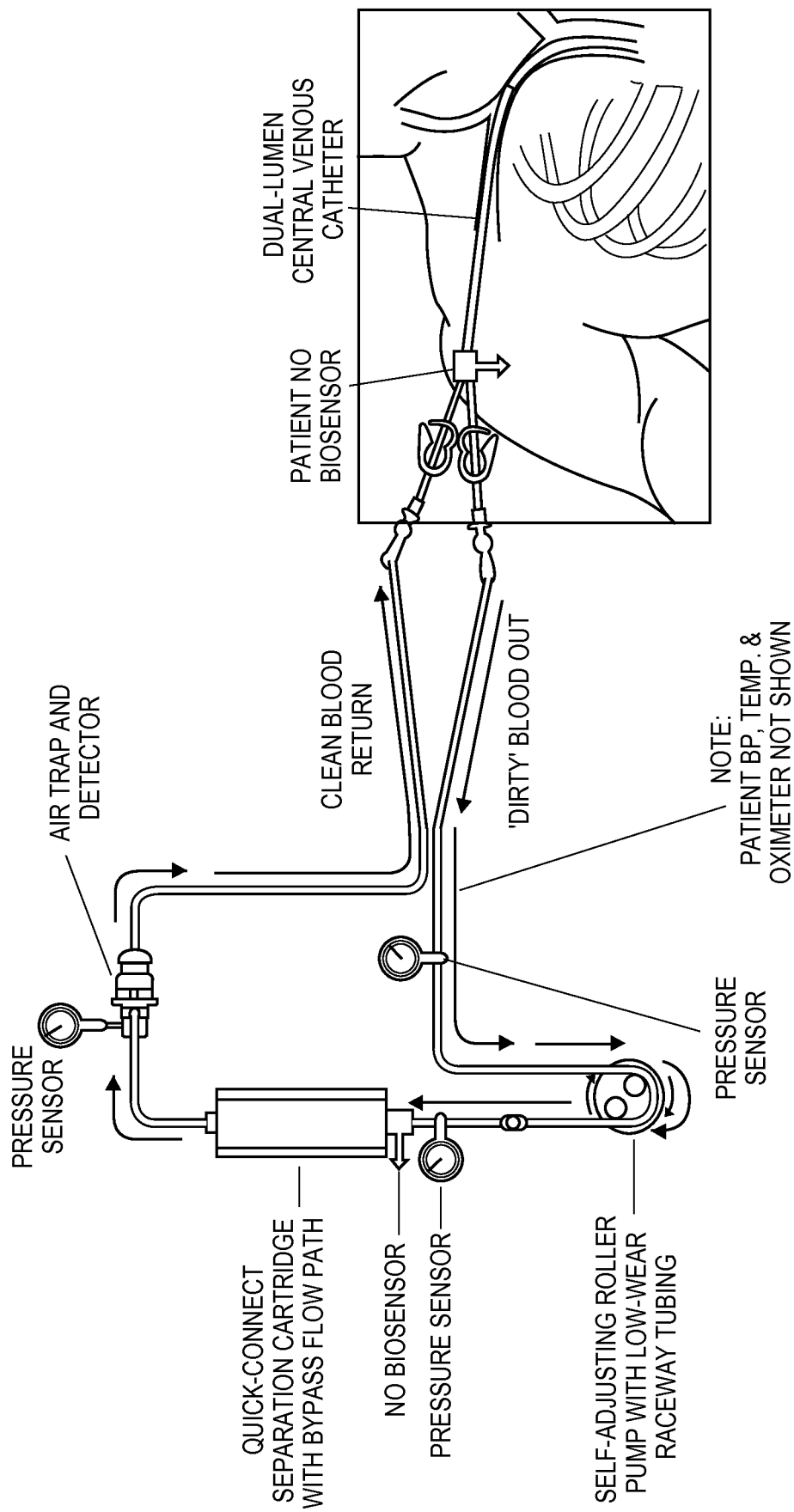
FIG. 1—Diagram of an embodiment of the present system.

Adsorbates in blood are conveyed to binding sites on the high-efficiency media by forced convection (a.k.a. advection), not slow diffusion through nano-porous particles or membranes. This allows binding of high-molecular-weight and cellular adsorbates at flows as high as 12 L/hr., and therefore reduced treatment time. The present DLT system may include new biosensors for bioavailable nitric oxide (NO), a biomarker in the progression of sepsis, via the quantification of NO released from its primary carrier molecules in blood. The present DLT system may also include other sensors for biomarkers of the onset and/or progression of sepsis in addition to or as alternatives to NO sensors.

The system of the present invention may be a self-powered unit which contains associated electronics. It may also include a blood pump that minimizes hemolysis and tubing wear.

In one embodiment the characteristics of cartridge pressure drop, biosensor output, patient and system data, are logged and trended for caregiver feedback and alarming, and are optionally available by telemetry.

In another embodiment, replacement or bypass of used cartridges is automated.

In another embodiment, the system of the present invention is effective against a significant number of blood-borne factors of interest, without the need to first identify specific pathogens. Thus, the present methods include a safe broad-spectrum, device-based approach to treat dysregulated inflammation and sepsis, in which multiple modes of action combat this complex disease process.

Another object of the invention is to provide a therapy for treating sepsis, particularly as caused by battle field trauma, by removing pathogens or toxins from a patient's blood by contacting the blood with a solid essentially nonporous substrate coated with heparin (and optionally other adsorbent molecules) and returning the blood to the patient suffering from the disease.

The above mentioned objects are not intended to limit the scope of the invention in any way.

DETAILED DESCRIPTION OF THE INVENTION

The present system safely reduces the concentration of pathogens and toxins in blood with a broad-spectrum biomimetic separation technology that mimics a common host/pathogen interaction. In one embodiment, whole blood is exposed to a high-surface area substrate functionalized with heparin, an analogue of heparan sulfate (HS), which is found on all cell membranes. HS may contribute to the prevention of clotting on the surfaces of healthy blood vessels. However, many (but not all) pathogens and toxins naturally bind to heparan sulfate to subvert the host's immune response and invade the body. Most inflammatory cytokines, such as TNF-α, GRO, and IL-8 also bind to heparin and heparan sulfate. In the present separation process heparin contributes to system efficacy, but it also provides system safety because the heparinized surfaces of the present system are the most anti-thrombogenic artificial surfaces known. This allows the system to be used without systemic anticoagulants even at fairly low flow rates. However, laminar flow through microchannels in the adsorbent bed and rapid adsorption kinetics also permit the present DLT to operate at higher flow rates (typical of many extracorporeal circuits), with reduced treatment times.

In one embodiment, the DLT system may include a catheter or other blood access device, a biosensor, and a broad-spectrum separation cartridge. In a particular embodiment the DLT system includes an acute blood access catheter, one or more novel nitric oxide biosensors, a self adjusting roller pump, a heparinized tubing set with low-wear raceway tubing and pre-installed pressure and temperature sensors, together with the replaceable broad-spectrum separation cartridge.

Impact

In an embodiment specific to sepsis, the present system's approach enables proactive treatment with the DLT system at the first signs of disease without awaiting target microbe identification with a universal biomarker for sepsis regardless of etiology, tied to a therapeutic measure that does not involve administration of potentially ineffective antibiotics with their inherent shortcomings and drug resistance concerns.

Methods for removing blood-borne factors of interest may be found in WO 2007/069983, Method for extracorporeal removal of a pathogenic microbe, WO 2008/157570—Device and method for restoration of blood, U.S. 61/265,675—Method for removing cytokines from blood with surface-immobilized polysaccharide, U.S. 61/302,826—Removal of virulence factors through extracorporeal therapy, U.S. 61/326,430—Method for removal of MRSA from blood. The entire contents of each of the above are hereby expressly incorporated by reference.

High-Flow Complex Fluid Manipulation

The laminar blood flow separation cartridge of the present invention operates at low pressure drop at >200 mL/min (12 L/hr). Micro-channels within close-packed adsorption media have a tight size distribution and constitute a controlled fraction of internal volume. Adsorption sites are located on the media surface, not within or behind nano-pores. This feature and high (e.g. 50-1500 mL/min) flow rate reduces treatment time to a few hours.

One of the present adsorbents is end-point attached heparin. It is considered the most antithrombogenic and biocompatible surfaces ever developed for blood-contacting devices. Heparin binds the coagulation inhibitor antithrombin, catalytically increasing its capacity.

End-point attached heparin has been used for other types of blood contacting devices and has been approved for clinical use. Examples of approved medical devices with covalently end-point attached heparin include:
1. Medtronic Maxima Oxygenator-Cardiopulmonary Bypass Circuit: CE Mark and FDA Approval
2. The Diametrics Paratrend Intravascular Blood Gas Sensor Catheter: CE Mark and FDA approved
3. The Pharmacia CeeOn Intraocular Lens: CE Mark and FDA Approval
4. The Berlin Heart ventricular assist devices EXCOR and INCOR: CE Mark
5. The Cordis Bx Velocity Coronary Stent Hepacoat: CE Mark and FDA Approval Heparan sulfate, a closely related substance, is present on all blood-contacting surfaces of the human vascular system where it contributes to the non-thrombogenic properties of blood vessel walls.

The negatively-charged hydrophilic surface causes minimal binding and activation of platelets (a.k.a. thrombocytes) and complement. The present system for a separation process not requiring systemic anticoagulation may be preferable to using so-called microfluidics for the bulk flow of blood treated by the DLT as a means for preventing clotting.

The large number of micro-machined channels needed to accommodate, e.g., 1200 mL/hr at shear rates that do not cause cell damage suggests that microfluidics technology would be reserved for use in sensors instead of the much higher flow rates of the main extracorporeal circuit.

The addition of other adsorbents besides heparin is very straightforward. For instance a candidate adsorbent media can be tested on an instrumented, bench-top mock circulation loop with a blood analogue. Adsorbent size distribution and the column packing, including the distribution of mixed adsorbent types within the column, is varied to achieve pressure drops comparable with the existing heparin-only column. If this pressure drop goal is not be met the column geometry is modified to reduce pressure drop, e.g., by increasing flow channel dimensions.

Unexpectedly Improved Aspects of the Biocompatible High-Flow Complex Fluid Manipulation:
1. Use of heparin for target binding also avoids surface-induced thrombosis reducing the risk of flow channel blockage and embolization from the separation cartridge
2. Treatment of all blood-contacting surfaces in the extracorporeal circuit with end-point attached heparin eliminates the need for systemic heparinization of the patient
3. The presence of heparinized adsorption media in close proximity to other less blood compatible adsorption media still renders the entire adsorbent bed blood compatible.
4. Use of surface-bound adsorption sites and forced-convection transport of adsorbates to binding sites permits high flow rates and increases adsorbtion efficiency
5. Lack of nano-pores in adsorbent media (or in an intervening membrane) gives high molecular weight targets and cellular adsorbates access to binding sites resulting in broad-spectrum functionality and rapid kinetics
6. Rigid hydrophobic media support/substrate (instead of a soft hydrophilic gel) resists compaction under flow, and thus reduces initial pressure drop and pressure drop increase during treatment
7. Microchannels of controlled size are easily created by close packing of rigid spherical media (optionally fused into a monolith) with a narrow size distribution. Lack of micromachining reduces cost and facilitates scale-up
8. Hyrophilicity of the present system's media promotes wetting by blood, reducing entry pressure of blood and aqueous fluids (e.g. saline) and facilitating initial de-airing of the separation cartridge Intrinsic Separation from Complex Fluid Another aspect of the present invention is an extracorporeal hemo-filter (adsorption cartridge) to safely remove the blood-borne factors of interest, such as pathogens, toxins, and pro-inflammatory cytokines for the treatment of sepsis and infectious diseases. The device is capable of removing many bacteria, viruses, toxins, and inflammatory molecules from human blood, which is then returned to the patient. Sepsis is a serious inflammatory disease is the result of severe and dysregulated inflammation during and after infection from pathogens such as *E. coli*, methicilin resistant *S. aureus* (MRSA), *B. anthracis* (anthrax), and *N. meningitides*. Other pathogens, ranging from viruses like dengue fever to parasites like *Plasmodium falciparum*, bind to the biologically active media and theoretically can also be removed from blood when used in a dialysis like therapy.

Substrates and their Qualities

The substrate or cartridge of the invention can specifically be prepared according to the following methods.

Cytokines or pathogens (the adsorbates) can bind to a solid, non micro-porous substrate which has been surface treated with an adsorbent, for example, polysaccharides, such as heparin, heparan sulphate, polyethylene imine (PEI), sialic acid, hyaluronic acid, and carbohydrates with mannose sequences, syndecans (transmembrane proteins that contain heparan sulphate proteoglycan segments (HSPGs) and are present on most cell types), or chemical groups (the adsorbent media) which have a binding affinity for the cytokine or pathogen.

In one embodiment the size of the interstitial channels within said media is balanced with the amount of media surface area and the surface concentration of binding sites on the media in order to provide adequate adsorptive capacity while also allowing relatively high flow rates of blood through the adsorbent media. The result is that transport of adsorbates to the binding sites on the media occurs largely by forced convection/advection. By (forced) convection is meant, for example, flow produced by a pressure gradient generated by a pump, by the application of external pressure to a flexible container (or internal pressure to a rigid container), by a gravity head/elevation difference, or by the difference in arterial pressure and venous pressure in the patient being treated. These substrates provide clinically-relevant adsorbtive capacity within the range of safe flow rates typically used in clinical extracorporeal blood circuits, e.g., in dialysis, cardiopulmonary bypass, and extra corporeal membrane oxygenation of blood. The method is in direct contrast to the much slower diffusive transport of adsorbates typically required with micro-porous or nano-porous adsorbent media, which require adsorbates to diffuse through membrane pores, and/or into pores below the surface of a solid media before binding to adsorption sites on, behind, or within the media, which therefore require very low flow rates to achieve significant separations during each passage of blood.

In one embodiment, heparin is immobilized onto the surface of the substrate. Immobilized heparin bound to a surface is effective for removing a significant amount of cytokines and pathogens from blood.

However, the flow rates typical of extracorporeal blood circuits require that the adsorbent 'bed' be designed to allow relatively high flow rates to operate safely. This is in part due to the universal tendency of slow-moving or stagnant blood to form dangerous clots. The substrate is designed with sufficiently large interstitial dimensions to permit a high flow rate of blood over the substrate without a large pressure drop. That is, as blood is taken from a mammalian patient, it is passed over the substrate at a flow rate whereby the delivery of adsorbates to the surface of the adsorbent bed is characterized primarily by forced convection/advection. This is in contrast to the much slower process of molecular diffusion that occurs in the use of highly porous adsorbent media (e.g. porous silica, sephadex, crosslinked polystyrene and other size exclusion media), and many other microporous media. Molecular diffusion is also required when selectively-permeable barrier membranes are used together with adsorption media, e.g., to prevent contact of the adsorption media by blood cells, bacteria, visruses, parasites and/or high molecular weight solutes during affinity therapy.

The binding of cytokines and pathogens by heparin and/or other adsorbent molecules during convection transport is particularly effective under the relatively high-flow conditions typically employed in the (safe) operation of extracorporeal blood circuits, e.g. when measured by linear flow velocity, ≥8 cm/min, preferably about ≥24 cm/min, and more preferably about 24-329 cm/minute, or, when measured by flow rate, around >50 mL/minute and preferably >150 mL/minute but less than about 2000 mL/minute.

Adsorption within the pores of microporous media, in contrast, may require much lower flow rates through adsorption beds of practical size in order to achieve an adequate separation or purification, i.e. <50 mL/min to as low as <1 mL/min.

It is recognized that, strictly speaking, it is 'residence time' on the adsorption column that needs to be much longer for a media requiring diffusive transport of adsorbates to the adsorbent site within the media, when compared to the lower residence time needed to convey an adsorbate to the binding site (on an essentially nonporous media) by forced convection/advection. However, there are practical limits to the dimensions of a safe and effective adsorbent cartridge, column, filter, etc., especially with respect to the maximum hold-up volume of blood it can contain, and the flow velocity of blood or serum past the adsorption media. For this reason average flow rate through the adsorption device is considered to be an important design variable.

Convection kinetics and diffusion kinetics can be compared in the removal of cytokines or pathogens from flowing blood: Adsorption media that depend on diffusion transport generally use very porous materials with extremely high internal surface area due to the presence of microscopic pores. Media suited for convection transport, on the other hand, generally rely on macroscopic "channels" or visible interstices between solid, essential nonporous material, such as particles, beads, fibers, reticulated foams, or optionally spiral-wound dense membranes.

Media that rely on forced convection transport are generally more suitable for high-flow rates, while media that rely on the much slower diffusion transport are much less effective when high flow rates and shorter residence times are required. For this reason, in an extracorporeal blood purification device, an adsorption media that does not require the adsorbate to slowly diffuse into pores within the adsorbent media is much preferred. When blood is pumped through circuits fabricated from man-made materials it is a general practice to employ relatively high blood flow rates in order to prevent stagnation and reduce the risk of clotting. On the other hand, extremely high flow rates must be avoided because they can expose blood cells to high shear rates and impingement damage that can rupture or otherwise damage blood cells. The present invention, therefore, provides a method and device for removing cytokines and/or pathogens from blood using the preferred characteristics of convection transport and its desirable, more-rapid kinetics. This is achieved by passing/flowing blood over an essentially non-microporous substrate that has been surface treated with adsorbent molecules, e.g. heparin, and which is therefore capable of binding the desired cytokine or pathogens to remove them from the blood. It is also possible to use a microporous substrate in the present invention if surface treatment renders that substrate effectively nonporous. This can occur intentionally or inadvertently, when surface treatments during media manufacturing block the pores to the passage of targeted adsorbates. This converts the microporous substrate to one that does not require diffusion of adsorbate into pores to bind to the media.

The substrates are intended to be applied primarily in extracorporeal therapies or procedures, although implantable devices are also possible. "Extracorporeal therapies" means procedures that are conducted outside the body, such as therapies in which desired products like oxygen, blood-anticoagulants, anesthetics etc. can be added to body fluids. Conversely, undesired products like naturally occurring toxins or poisons can be also removed from body fluids with specific types of extracorporeal circuits. Examples are haemodialysis and haemofiltration which represent technologies whereby blood is depleted of waste products. Adsorption on activated carbon has been used to remove blood-borne poisons, and so forth.

Whole blood and blood serum from mammals can be used in the present invention. The amount of blood or blood serum that can be used in the claimed methods is not intended to be limited. It can range from less than 1 mL to above 1 L, up to and including the entire blood volume of the patient when continuous recirculation back to the patient is employed. One or more 'passes' through the adsorption bed may be used if needed. The blood may be human or animal blood.

Adsorption media to remove cytokines or pathogens from blood are optimized for use in traditional extracorporeal blood circulation with flow rates>50 mL/min, and preferably between about 150 and 2000 mL/min. If measured by linear flow velocity, ≥8 cm/min, preferably about ≥24 cm/min and more preferably about 24-329 cm/min. Such high flow rates create short residence times within the adsorption column and convection transport dominates over Brownian diffusive transport. This is particularly important for binding large MW proteins or cytokines such as TNF-α and larger particles such as viruses, bacteria and parasites because they diffuse very, very slowly. In the present invention the dominant adsorption sites available for removing cytokines and pathogens lie at the surfaces within the interstices of the media bed through which the blood flows or is delivered by forced convection. To treat blood, the interstitial channels need to be large enough to allow the transport of red blood cells, which are an average 6 microns in diameter. To allow a packed adsorption cartridge to be placed into an extracorporeal circuit with high blood flow rate, the interstitial channels must be several times larger than the diameter of red blood cells. This can prevent high shear rates that lead to hemolysis while simultaneously minimizing pressure drop in the blood that flows through the packed bed or cartridge. Additionally, the media is preferably rigid to minimize deformation that could clog the filter cartridge by compaction. Based on these preferences, an optimized rigid media balances interstitial channel size and total surface area, e.g., for efficient removal of pathogens and/or cytokines in high-flow extracorporeal blood circuits.

Substrate Materials

Various materials, in shape and composition, can be used in a substrate or cartridge. All suitable substrates provide high surface area while promoting the conveyance of adsorbates to the adsorbent sites that bind them (primarily) by forced convective transport. The media is typically provided packed within a container, such as a column, that is designed to hold the media so that it will not be carried away in the flowing blood (a.k.a. media migration) and permit the flow of blood past essentially all of the media's surface. Useful substrates for creating the adsorption media include non-porous rigid beads, particles, or packing, reticulated foams, a rigid monolithic bed (e.g. formed from sintered beads or particles), a column packed with woven or non woven fabric, a column packed with a yarn or solid or hollow dense (not microporous) monofilament fibers, a spiral wound cartridge formed from flat film or dense membrane, or a combination of media such as a mixed bead/fabric cartridge. A suitable substrate is one that is initially microporous but becomes essentially nonporous when the surface is treated before, during or after the creation of adsorption sites, e.g., via end-point-attached heparin.

The column has a macroporous structure that presents a high surface area to the blood or serum while preventing a large pressure drop and high shear rates. In addition to the potential for damaging the blood by hemolysis, high pressure drops should be avoided because they can shut down extracorporeal circuits equipped with automatic shut offs that respond to pressure drop.

The substrate may also take the form of a dense barrier membrane. In this embodiment, the surface of a non-porous film is modified by binding heparin, heparan sulphate or another adsorbent polysaccharide together with optional adsorbing groups not derived from heparin, heparan sulphate, or the adsorbent polysaccharide to the membrane's surface. Alternatively, a microporous membrane may be rendered nonporous or 'dense' before, during or after attachment of binding sites by filling the pores with essentially non-porous material, e.g., a polymer. The membrane in sheet or (hollow) fiber form may be arranged within a housing to present high surface area for blood contact.

Beads as Substrate

One useful substrate is in the form of solid beads or particles. The 'beads' can be made of materials that are sufficiently rigid to resist deformation/compaction under the encountered flow rates. Resistance to deformation is necessary to maintain the free volume and subsequent low pressure drop of the packed bed 'contactor'. The substantial lack of accessible pores in the bulk of the substrate eliminates the need for adsorbates to diffuse into the pores prior to adsorption. The adsorption sites of the present invention are primarily on the surface of the media and are thus positioned to be accessible to adsorbates in the blood delivered to that surface largely by convective transport. Suitable substrates need not be perfectly smooth on their surface since roughness produces a desirable increase in surface area for attachment of binding sites, e.g. by covalent or ionic bonding of heparin. Accessible internal pores with molecular dimension, on the other hand, are largely avoided to eliminate the need for adsorbates to diffuse into the pores before attaching to binding sites.

Various kinds of beads can be used as the substrate. Useful beads should have sufficient size and rigidity to avoid deformation/compaction during use in the method, and have sufficient surface area to be capable of being coated with heparin for use in the method.

Evidence of sufficient substrate rigidity is the absence of a significant increase in pressure drop across the adsorption bed during about one hour of flow of water or saline at rates typical of clinical use: for example, <10-50% increase relative to the initial pressure drop (measured within the first minute of flow) when measured at similar flow rate, e.g, of saline.

The beads or other high-surface-area substrates may be made from a number of different biocompatible materials, such as natural or synthetic polymers or non-polymeric material including glasses, ceramics and metals, that are essentially free of leachable impurities. Some exemplary polymers including polyurethane, polymethylmethacrylate, polyethylene or co-polymers of ethylene and other monomers, polyethylene imine, polypropylene, and polyisobutylene. Examples of useful substrates include nonporous Ultra High Molecular Weight PolyEthylene (UHMWPE). Other suitable beads are polystyrene, high density and low density polyethylene, silica, polyurethane, and chitosan.

Methods for making such beads are known in the art. Polyethylene beads and other polyolefin beads are produced directly during the synthesis process and can often be used without further size reduction. Other polymers may need to be ground or spray dried and classified, or otherwise processed to create beads of the desired size distribution and shape.

As noted above, the size of the channels or interstitial space between individual beads for extracorporeal blood filtration should be optimized to prevent a high-pressure drop between the inlet and outlet of the cartridge, to permit safe passage of the blood cells between the individual beads in a high flow environment, and to provide appropriate interstitial surface area for binding of the polysaccharide adsorbent to the cytokines or pathogens in the blood. In a close packed bed of 300-micron, roughly spherical beads, an appropriate interstitial pore size is approximately 68 microns in diameter. Useful beads have a size ranging from about 100 to above 500 microns in diameter. The average size of the beads can be from 150 to 450 microns. For example, polyethylene beads from Polymer Technology Group (Berkeley, USA) having an average diameter of 0.3 mm are suitable. The interstitial pore is a function of bead size.

For use, the suitable beads are housed in a container, such as a column. Other suitable forms of substrate are described below.

Reticulated foams have open cells and can be made from, for example, polyurethanes and polyethylenes. Control of pore size can be achieved by controlling the manufacturing method. In general, reticulated foams can have between 3 and 100 pores/inch and can exhibit a surface area of ≥66 $cm^2/cm^3$.

Beads can be sintered into a monolithic porous structure through either chemical or physical means. Polyethylene beads can be sintered by heating the beads above their melting temperature in a cartridge and applying pressure. The resulting interstitial pore size is slightly reduced from the interstitial pore size of a packed bed of non-sintered beads of equal size. This reduction can be determined empirically and used to produce the desired final interstitial pore size.

A column or other housing shape can be packed with either woven or non-woven heparinized fabric or the heparin, heparan sulphate or optional non-heparin adsorption sites may be attached, e.g. by covalent, ionic or other chemical or physical bonds, after the housing has been filled with the substrate media. By controlling the fiber denier and density of the fabric during weaving or knitting or during the creation of a non-woven web, the interstitial pore size can be controlled. Useful non-woven fabrics may be in the form of felts, melt-blown, or electrostatically spun webs, having a random orientation held together by entanglement of the fibers and/or adhesion or cohesion of intersecting fibers. Useful woven fabrics have a more defined and non-random structure.

A column can be packed with fibers or yarns made from fibers. Polyethylene, and other fibers, can be drawn into thin hollow or solid monofilament fibers or multifilament yarns, that can be packed into cartridges in the same way that hollow fiber membranes are installed within conventional hemodialysis cartridges or blood oxygenators. Originally porous hollow fibers are rendered dense or non-porous before, during or after binding heparin or other adsorbents to the outer and/or inner surfaces. Dyneema Purity® from Royal DSM is a high-strength solid fiber made of UHMWPE. Dyneema can be heparinized and packed into a cartridge to provide a high-surface area support for the removal of cytokines and pathogens.

A spiral wound cartridge contains a thin film or membrane that is tightly wound together with optional spacer materials to prevent contact of adjacent surfaces. The membrane can be made from polymers such as polyurethane, polyethylene polypropylene, polysulfone, polycarbonate, PET, PBT, etc.

Attachment of the Adsorbant Polysaccharide

The adsorbant polysaccharide can be bound to the surface of the solid substrate by various methods, including covalent attachment or ionic attachment.

The adsorption media can comprise heparin covalently linked to the surface of the solid substrate. Various per se known methods can be used to attach heparin to the desired substrate, such as described in a review article by Wendel and Ziemer. (H. P Wendel and G. Ziemer, European Journal of Cardio-thoracic Surgery 16 (1999) 342-350). In one embodiment, the heparin is linked to the solid substrate by covalent end-point attachment. This method increases the safety of the device by reducing or eliminating the release of heparin from the substrate surface that could enter the blood stream. 'Leaching' of heparin by and into the blood is to be avoided because it can increase the risk of bleeding and heparin-induced thrombocytopenia.

Covalent attachment of the polysaccharide, such as heparin, to a solid substrate provides better control of parameters such as surface density and orientation of the immobilized molecules as compared to non-covalent attachment. These parameters have been shown by the inventors to be important in order to provide optimal cytokine or pathogen binding to the immobilized carbohydrate molecules. The surface concentration of heparin on the solid substrate can be in the range of 1-10 µg/cm$^2$. Covalent end-point attachment means that the polysaccharide, such as heparin is covalently attached to the solid substrate via the terminal residue of the heparin molecule. Heparin can also be bound at multiple points. The end-point attachment is preferred.

If beads are used, they may be hydrophilized prior to attachment of the polysaccharide, such as heparin, or other compound. Possible methods of preparing the beads include acid etching, plasma treating, and exposure to strong oxidizers such as potassium permanganate.

Amount of Polysaccharide/Gram Substrate

The amount of polysaccharide adsorbent per gram substrate can vary. In one particular embodiment, if beads are used, the amount of polysaccharide, such as heparin per gram bead is determined by the number of layers used and also the size of the beads. The larger the bead, the less polysaccharide, such as heparin per gram of bead is achieved. One preferred amount is 2.0±0.5 mg heparin/g bead per the MBTH method.

The molecular weight of polysaccharide used in the claimed methods can vary. For example, native heparin has an average molecular weight of 22 kDa. Nitric acid degraded heparin has a molecular weight of 8 kDa. Synthetically produced polysaccharides may also be used. They may have a uniform or diverse molecular weight.

The absorption be may be prepared from a mixture of heparinized media and other media, e.g., media which is inherently thrombogenic. By assembling an adsorption cartridge with both heparinized surfaces and, for example, cationic surfaces (or other inherently thrombogenic surfaces), cytokines, pathogens, and endotoxins can all be safely removed from blood or biological fluid.

Another biologically active, but thrombogenic carbohydrate is sialic acid. Sialic acid is known to bind virus lectins, including influenza. (C, Mandal. 1990, Experientia, Vol. 46, pp. 433-439, *Sialic acid binding Lectins.*) A mixed cartridge of heparinized beads and sialic acid coated beads can be useful in treating patients, such as during an influenza pandemic.

Abdominal septic shock, as discussed above, is usually caused by *E. coli* which is a gram negative bacterial. Gram negative bacteria typically do not bind to heparin, and therefore it would be useful to have an adsorption column with multifunctionality to bind these bacteria in addition to cytokines and/or endotoxins. Carbohydrates with mannose sequences, such as methyl α-D-mannopyranoside, are known to bind *E. coli, K. pneumonia, P. aeruginosa*, and *Salmonella*. (Ofek I., and Beachey E. H. 1, 1978, Infection and Immunity, Vol. 22, pp. 247-254, *Mannose Binding and Epithelial Cell Adherence of Escherichia coli* and Sharon, N. 2, 1987, FEBS letters, Vol. 217, pp. 145-157 *Bacterial lectins, cell-cell recognition and infectious disease.*)

The use of this embodiment is based on the concept that an antithrombogenic surface in intimate contact with, or in close proximity to a thrombogenic surface can prevent clinically significant thrombus formation that would otherwise occur if the inherently thrombogenic surface was used alone. In the case of adsorption media in the form beads or particles a it is preferred to blend the different adsorption media together before packing them into a cartridge or other housing. This provides intimate contact among the various surface chemistries on adjacent beads while permitting efficient manufacturing of adsorption cartridges or filters. A related approach is to layer the different media in a 'parfait-type' arrangement within the housing such that the blood contacts the different media in series or parallel flow. One arrangement of the different media within a cartridge is to position unblended antithrombogenic media at the entrance and/or the exit of the cartridge, with an optionally blended region containing the more thrombogenic media interposed between the entrance and exit regions. In the case of media in fiber form, a mixed woven, knitted, or nonwoven structure can be prepared by methods well known in the textile industry to form fabric from the mixed fiber. Alternatively a yarn can be prepared from finer multifilament yarn or monfilment made from two or more fibers with different surface chemistries, as long as one fiber type contains a surface that actively prevents blood clotting on contact. The mixed-fiber yarn can then be used to prepare fabric for blood contact. Hollow fiber or solid fiber adsorption media can be blended and used to make cartridges that resemble hollow-fiber dialyzers or oxygenators. For membrane or film-type adsorption media of the type that is used in a spiral-wound adsorption cartridges, two or more surface chemistries may be used in close proximity to each other such that the blood must contact both surface chemistries (nearly) simultaneously. This could be done with a regular or random array of the various binding groups within the surface layer of the membrane film, or by forming a flow path for blood between two closely-spaced membrane films, one of which is antithrobogenic.

3. Mixture of Substrate Materials with Different Surface Functionality

In addition to heparin and heparan sulfate, there are other biologically active chemical moieties including other carbohydrates that can remove harmful substances from blood and biological fluids that are not efficiently removed by immobilized heparin alone. For example, chitosan, a highly cationic, positively-charged carbohydrate will bind endotoxins. Other positively charged molecules, such as polyethylene imine (PEI), can also bind endotoxins. However, cationic surfaces are significantly less blood compatible than heparinized surfaces and can lead to increased thrombogenicity, a dangerous condition in blood contacting devices. (See Sagnella S., and Mai-Ngam K. 2005, Colloids and Surfaces B: Biointerfaces, Vol. 42, pp. 147-155, *Chitosan* based surfactant polymers designed to improve blood compatibility on biomaterials and Keuren J. F. W., Wielders S. J. H., Willems G. M., Mona M., Cahalan L., Cahalan P., and Lindhout T. 2003, Biomaterials, Vol. 24, pp. 1917-1924. *Thrombogenecity of polysaccharide-coated surfaces*). While it is possible to use an adsorption cartridge containing PEI, chitosan or other inherently throbogenic surfaces as a bioactive adsorbent to remove LPS or endotoxins from blood, due to the severe clotting risk, the patient would need a high dose of systemic anticoagulant. In the case of systemic heparin, this could lead to a bleeding risk and possible thrombocytopenia.

The adsorption bed is prepared from a mixture of heparinized media and media which is inherently thrombogenic. By assembling an adsorption cartridge with both heparinized surfaces and, for example, cationic surfaces (or other inherently thrombogenic surfaces), cytokines, pathogens, and endotoxins can all be safely removed from blood or biological fluid.

Device/System

Another aspect of the present invention provides use of a device comprising the adsorbent modified solid substrate, the adsorbent having a binding affinity for a cytokine or pathogen, for extracorporeal removal of the cytokine or pathogen from mammalian blood.

A device may comprise a conventional device for extracorporeal treatment of blood and serum from patients, e.g. suffering from renal failure.

Local blood flow patterns in blood contacting medical devices for extracorporeal circulation are known to influence clot formation via shear activation and aggregation of platelets in stagnant zones. Consequently, a device should be designed in a fashion that does not create these problems.

A device may for example have the following properties:
A blood flow in the range of 150-2000 ml/min, or if measured by linear flow velocity of ≥8 cm/min.
Low flow resistance.
Large surface area of substrate having carbohydrates immobilized thereto, e.g. about 0.1-1 m².
Stable coating (no clinically significant leakage of carbohydrate to the blood in contact therewith).
Proper haemodynamic properties in the device (no stagnant zones).
Optimal biocompatibility.

The device/system of the invention includes a blood pump to pump the patient's blood through filter cartridge. Various known blood pumps can be used in the invention, particularly adapted for use in the field, such as on a battlefield. Useful pumps can include a Power Infuser, from Infusion Dynamics. Another non-limiting example of such a device is a pediatric haemoflow dialyzer which is an extracorporeal blood filtration device for removing cytokine molecules and which is compatible with high flow rates. One such device is available from Exthera Medical. Other models or types of devices for extracorporeal treatment of blood or serum may also be used, such as the Prisma M 10 haemofilter/dialyzer from Gambro AB, Sweden. Additionally, specially adapted blood pumps or specially designed blood pumps may be used.

High-flow conditions can be defined as blood flow above the diffusion limit.

The device/system of the invention also may include one or more suitable biosensor(s). These biosensors can be known and commercially available sensors used with complex biological fluids, such as blood, to detect pathogens, toxins and other biomolecules. The sensors specifically are capable of detecting pathogens, toxins and other biomolecules in the circulating blood of a patient, or in blood samples and components. Useful biosensors are self-contained integrated devices that can provide quantitative or semi-quantitative analytical information using a biological recognition element. On the battlefield, for example, biosensors could be placed on the body of a soldier, built into the clothing/uniform or contained in/on a small device on the soldier, wherein receptors in the biosensor would bind to a pathogen or toxin.

Blood-Borne Components Removable by the Invention

The "Dialysis Like Therapy" (DLT) of the present invention can remove blood-borne pathogens, toxins, and inflammatory cytokines for the treatment of sepsis and infectious diseases by capturing many bacteria, viruses, toxins, and inflammatory molecules from blood. Key characteristics of the invention include:

1. Broad spectrum—Binds many inflammatory cytokines, bacteria, viruses, parasites, toxins, and clotting factors.
2. Fast kinetics—Uses fast convective transport, not slow diffusion through a microporous media
3. Systemic anticoagulants are optional—End-point attached heparin is anti-thrombogenic and non-leachable: the 'gold standard' for blood-contacting surfaces
4. Low Pressure Drop—Compatible with conventional, and field-ready blood pumps
5. Scalable—low-cost manufacturing Cytokines As used herein, the term "cytokine" means a protein, released for instance in connection with microbial infection or immunization, selected from the group consisting of interleukins, interferons, chemokines and tumour necrosis factors. Examples of the cytokine(s) are vascular cell adhesion molecule (VCAM), antithrombin, Regulated on Activation Normal T Expressed and Secreted protein (RANTES), interferon, tumor necrosis factor alpha (TNF-alpha), tumor necrosis factor beta (TNF-beta), interleukin-1 (IL-1), IL-8, GRO-α and interleukin-6 (IL-6).

The method also provides for the selective removal of cytokines from the blood by strongly adsorbing heparin-binding molecules. Some molecules have a higher binding affinity for heparin than others. For example, TNF-α has a high affinity for heparin.

Pathogens

An additional aspect of the invention provides a method of treating a disease by removing cytokines and/or pathogens from mammalian blood by contacting mammalian blood with the solid substrate disclosed in the method above. Examples of pathogens that can be removed from the blood using heparinized substrate according to the invention include:

Viruses—Adenovirus, Coronavirus, Dengue virus, Hepatitis B, Hepatitis C, HIV, HPV Cytomegalovirus, and others.

Bacteria—*Bacillus anthracis, Chlamydia pneumoniaem, Listeria monocytogenes, Pseudomonas aeruginosa, Staphylococcus aureus*, MRSA, *Streptococcus pyrogenes, Yersinia enterocolitica*, and others Parasites—*Giardia lambitia, plasmodium* spp. and others. See also, Chen, Y. Gotte M., Liu J., and Park P. W., Mol. Cells, 26, 415-426.

For instance, treatment of infections caused by any of the following three pathogens can remove, partially or fully the following toxins from the blood:

a) for *B. anthracis*
The Tripartite Protein toxin (Anthrax toxin) comprising
Protective antigen (PA)
Edema factor (EF)
Lethal factor (LF)

Polyclutamic acid capsule
Anthralysin O (AnlO)
Anthralysin B (AnlB)
Lethal toxin (LT)
b) for *B. aureus*
α-toxin
β-toxin
c) for *P. aeruginosa*
Las A The following are examples of categories and specific potential biomarkers suitable for treatment with a DLT sensor:

Pathogenic
  Bacterial
    Bacterial Cells
    Bacteria DNA (PCR detection methods)
    Exotoxins
      PA
      A-toxin
      Las-A
    Endotoxins
      LPS
  Viruses
    HIV
    Hep-C
    Dengue
    Viral hemorrhagic fevers
    Cytomegalovirus
  Parasites
    Malaria
  Fungi
    *Candida*
Cytokines/chemokines
  GRO-α
  TNF-α
  IL-6
  RANTES
Coagulation
  D-dimers
  Fibrin
  Protein C
Vascular Damage
  ADAMST-13
  Angiopoietin
Vasodilation
  NO, nitrate, nitrite
Organ Disfunction
  Bilirubin
  Creatinine
  Lactate
Acute phase protein
  C-reactive protein (CRP)
  Lipopolysaccharide binding protein
  PCT
Complement
  C3
  C4
  C5a Diseases to be Treated As noted above, one example of a disease to be treated according to the invention is anthrax. In most cases, early treatment can cure anthrax. The cutaneous (skin) form of anthrax can be treated with common antibiotics such as penicillin, tetracycline, erythromycin and ciprofloxacin (Cipro). The pulmonary form of anthrax is a medical emergency. Early and continuous intravenous therapy with antibiotics may be lifesaving. In a bioterrorism attack, individuals exposed to anthrax will be given antibiotics before they become sick. A vaccine exists but is not yet available to the general public. There are three forms of disease caused by anthrax: cutaneous (skin) anthrax, inhalation anthrax and gastrointestinal (bowel) anthrax. Inhalation anthrax is a very serious disease, and unfortunately, most affected individuals will die even if they get appropriate antibiotics. Antibiotics are effective in killing the bacteria, but they do not destroy the deadly toxins that have already been released by the anthrax bacteria.

The methods of the present invention can be employed either before or after other conventional treatments, such as administration of antibiotics.

Another example of a disease to be treated according to the invention is sepsis. Sepsis is generally considered to be a systemic response to an infection which can lead to organ failure and often death. The condition can be triggered by a bacterial, viral, parasitic or fungal infection. The condition is known to be particularly dangerous in hospitals where patients may already be immuno-compromised. During sepsis, the patient experiences a so-called cytokine storm and the body's immune system attacks healthy tissue that leads to multiple organ failure in highly perfused organs. Reducing TNF-α and other inflammatory molecules will modulate the immune response and could act as an organ preservation strategy. Additionally, any heparin-binding pathogens in the blood can be removed which would help reduce further colonization and could reduce the amount of antibiotics needed to treat an infection. This could improve patient safety by reducing side effect risks associated with antibiotic therapy.

The methods of the present invention can be employed either before or after other conventional treatments, such as administration of antibiotics.

Combining the Inventions with Additional Filtration/Separation Steps

In an embodiment of the treatment method, the extraction and reintroduction of blood may be performed in a continuous loop, which loop comprises a part of the bloodstream of the subject.

In a further aspect the methods described above can be combined with other methods to filter or treat mammalian blood. For example, a cartridge that is based on convection kinetics can then be used in series with conventional extracorporeal circuits such as CPB, hemodialysis, and oxygenation.

Further discussion of cartridges may be found in WO 2007/069983, WO 2008/157570, U.S. 61/265,675, U.S. 61/302,826, U.S. 61/326,430, and U.S. 61/443,236.

Unlike more thrombogenic (size exclusion and cationic adsorption) media, heparin binds adsorbates of all sizes, including cellular pathogens, without inducing clotting or significant activation of macrophages, granulocytes or complement. The present system does not use nano-porous membranes, or media that requires very slow diffusion of adsorbates to reach binding sites deep within the media. Instead the present system uses forced convection to rapidly deliver adsorbates to surface sites on the media. This permits high flow rates and reduces treatment times to ca. two hours or less.

The present system includes both a substrate based on micro-scale modification, and a nano-scale modification, in which new adsorbent sites are created on the media surface adjacent to heparin molecules. Separation cartridges containing the enhanced broad-spectrum media bind a broad spectrum of pathogens, toxins and biomolecules while maintaining the anti-thrombogenicity of the all-heparin surface.

Nitric Oxide

The Role of Nitric Oxide in Sepsis

Various biomarkers have been identified as being associated with sepsis and potentially useful as biomarkers to evaluate sepsis. Such biomarkers include NO, endotoxin and the pro-inflammatory cytokines IL-1b, IL-2, IL-6, TNF and interferon. See, Pierrokas et al., *Sepsis biomarkers: a review*; Critical Care 2010, 14:R15.

I. Continuous Sensing in a Complex Fluid

The ideal biomarker for use in a practical sepsis DLT system should be rapidly analyzed and have diagnostic, prognostication and therapy management value to influence critical physician decisions.

Furthermore, microfluidic biosensor engineering; vascular biology, sepsis modeling, algorithm development and biostatistical expertise can be incorporated into the present system to allow for on the spot data correlation and analysis and analysis by telemetry.

System Support

In one embodiment the present system is contained within a rugged, self-powered unit to be compact, light-weight, and energy efficient.

In additional embodiments, the DLT System also includes data logging, trending, and alarming for caregiver feedback based on biosensor output, cartridge pressure drop, and e.g., blood gas, temperature, and blood pressure.

Pressure readings, biosensor outputs, patient temperature, blood gas, blood pressure and system information is available by telemetry, and may be logged and trended graphically for caregiver feedback and alarming.

In one embodiment, system automation includes bypassing and replacing spent separation cartridges and sensors. Therefore, automatic replacement or bypass of expended cartridges may be predicted from regression of pressure drop vs. time and pump speed data for alarming and activating bypass valves.

As data sets and patient outcomes are accumulated from a number of human cases and stored on remote servers, they are available for analysis and use in future predictive models.

In one method of using the present system, early prophylactic use of the DLT system, even before positive identification of the responsible pathogen is indicated. The result is reduced morbidity and mortality for the wounded patients.

EXAMPLES

The various aspects of the invention are further described in the following examples. These examples are not intended to be limiting. For instance, in the present examples heparin is used. However, other carbohydrates and polysaccharide adsorbents may be used alone or in addition to the heparin-coated substrates exemplified below.

Example 1

Preparation of Heparin Column

Polyethylene (PE) beads, with an average diameter of 0.3 mm (lot no. 180153), are supplied by the Polymer Technology Group (Berkeley, USA) and the columns (Mobicol, 1 mL) are obtained from MoBiTec (Germany). Heparin and polyethyleneimine (PEI) are purchased from Scientific Protein Laboratories (Waunakee, Wis., USA) and BASF (Ludwigshafen, Germany) respectively. All chemicals used are of analytical grade or better.

Immobilization of heparin onto the beads was performed as described by Larm et al. (Larm O, Larsson R, Olsson P. A new non-thrombogenic surface prepared by selective covalent binding of heparin via a modified reducing terminal residue. *Biomater Med Devices Artif Organs* 1983; 11: 161-173).

The polymeric surface was heparinized using the general procedure described below.

The polymeric surface is etched with a oxidizing agent (potassium permanganate, ammoniumperoxidisulfate) in order to introduce hydrophilic characteristics together with some reactive functional groups (—$SO_3H$, —OH, —C═O, —C═C—). The surface can also be etched with plasma or corona. For example, the PE-beads are etched with an oxidizing agent (potassium permanganate in sulphuric acid). These hydrophilized beads, inter alia containing OH-groups and double bonds, are later used as controls.

Reactive amino functions are introduced by treatment with a polyamine, polyethylenimine (PEI) or chitosan. For some purposes the polyamines may be stabilized on the surface by cross linking with bifunctional reagents, such as crotonaldehyde or glutaraldehyde.

The coating is further stabilized by ionic cross linking with a sulfated polysaccharide (dextran sulfate or heparin). If necessary these steps are repeated and a sandwich structure is built up. Careful rinsing (water, suitable buffers) should be performed between each step. After a last addition of PEI or chitosan, end-point attachment (EPA) to the aminated surface of native heparin is done by reductive amination, utilizing the aldehyde function in the reducing terminal residue in native heparin.

A more reactive aldehyde function in the reducing terminal residue can be achieved by partial, nitrous degradation of heparin. This shortens the reaction time, but the immobilized heparin will have a lower molecular weight. The coupling is performed in aqueous solution, by reductive amination (cyanoborohydride, $CNBH_3^-$).

In this alternate method, the aminated media is suspended in acetate buffer (800 ml, 0.1 M, pH 4.0) and 4.0 g nitrous acid degraded heparin (heparin from Pharmacia, Sweden) was added. After shaking for 0.5 h, $NaBH_3CN$ (0.4 g) was added. The reaction mixture was shaken for 24 h and then processed as above, yielding heparinized media.

1-10 µg/cm$^2$ of heparin can be coupled to all hydrophilic surfaces like glass, cellulose, chitin etc, and more or less all hydrophobic polymers like polyvinyl chloride, polyethylene, polycarbonate, polystyrene, PTFE etc.

The resulting PE-beads, with covalently end-point attached heparin, are sterilized with ethylenoxide (ETO) and rinsed with 0.9% sodium chloride and ultra pure water. The amount heparin was determined to be 2.0 mg heparin/g bead with the MBTH method. (Larm O, Larsson R, Olsson P. A new non-thrombogenic surface prepared by selective covalent binding of heparin via a modified reducing terminal residue. Biomater Med Devices Artif Organs 1983; 11: 161-173 and Riesenfeld J, Roden L. Quantitative analysis of N-sulfated, N-acetylated, and unsubstituted glucosamine amino groups in heparin and related polysaccharides. Anal Biochem 1990; 188: 383-389).

The polyethylene beads that are used had a mean diameter of 0.3 mm and are heparinized with a technology that guaranteed that the heparin molecules are covalently end point attached to the surface, thereby making the carbohydrate chains more accessible for proteins with affinity for heparin/heparan sulphate. The mean molecular weight of the immobilized heparin was about 8 kDa, while 2 mg (equal to approximately 360 IU) was coupled to each gram of beads.

The integrity of this surface was verified by the expected removal of 75% of antithrombin (AT) concentrations from the blood passed over heparinized, but not non-heparinized, beads.

These data corresponds well with the previous observations from extracorporeal lung assistance (ECLA) on septic patients using surface heparinized oxygenators published by Bindslev et al. (Bindslev L, Eklund J, Norlander O, Swedenborg J, et al. Treatment of acute respiratory failure by extracorporeal carbon dioxide elimination performed with a surface heparinized artificial lung. *Anesthesiology* 1987; 67: 117-120.)

Example 2

Patients

The study protocol was approved by the local ethics committee at the Karolinska University Hospital and signed informed consent was obtained from each patient. Arterial blood was drawn from the hemodialyzers of three septic (fever>38° C., chills, leukocytes>12×10$^9$ cells/L) patients (2M/1F, aged 43, 56 and 68 years; Table 1).

TABLE 1

Clinical characteristics of patients donating blood.

| Patient | Sex | Age (years) | Body temperature (° C.) | Heart rate (beats/min) | Mean arterial pressure (mmHg) | Respiratory rate (breaths/min) | White blood cell count (10$^9$/L) |
|---|---|---|---|---|---|---|---|
| 1 | M | 43 | 39.2° | 110 | 76 | 20 | 19.0 |
| 2 | M | 56 | 38.6° | 90 | 95 | 18 | 17.5 |
| 3 | F | 68 | 38.5° | 100 | 89 | 21 | 19.5 |

The patients are previously administered with broad-spectrum antibiotics (ceftazidime or cefuroxime together with an aminoglycoside; one dose of each) and heparin (200 IU/kg body weight at the start of the dialysis). The blood was collected in EDTA vacuum tubes and immediately transferred to an adjacent room where 1 mL was applied to the previously prepared columns and passed through using a roller-pump at one of 1, 5 and 10 mL/min. Blood that had passed through the columns was immediately collected at the other end and cold-centrifuged (4500 G). The supernatants are subsequently collected and frozen at −80° C. for later analysis.

Example 3

Quantitative Analysis of Cytokines

The amounts of cytokines are determined using photoluminescence with a plate reader (Multiskan Ascent). Each sample was measured in three wells, and the geometric mean used for analysis. The intraassay coefficient of variation was below 8% for all kits. We used Coamatic antithrombin kit (Haemochrom, cat #8211991), Quantikine Human IL-6 (R&D Systems, cat #D6050), Quantikine Human IL-10 (R&D Systems, cat #D1000B), Protein C Antigen Test 96 (HL Scandinavia AB, product #H5285), Human CCL5/RANTES Quantikine (R&D Systems, cat #DRN00B), Quantikine Human sVCAM-1 (CD106) (R&D Systems, cat #DVC00), Quantikine Human IFN-gamma (R&D Systems, cat #DIF50), Quantikine HS TNF-alpha/TNFSF1A (R&D Systems, cat #HSTA00D) and BD OptEIA Human C5a ELISA Kit II (BD Biosciences, cat #557965).

Statistical Evaluation

Paired Kruskal-Wallis test was used to compare the before and after column blood concentrations of each cytokine, with a two-tailed p-value below 0.05 indicating significance. The results are summarized in Table 2.

TABLE 2

Concentrations of measured cytokines before and after blood passage through different columns.

| Cytokine | Before passage | Control beads After passage | p-value | Heparinized beads After passage | p-value |
|---|---|---|---|---|---|
| | | 10 g beads/1 mL blood | | | |
| VCAM (ng/mL) | 115.5 | 99.0 (−14%) | 0.30 | 88.8 (−23%) | <0.05 |
| IL-6 (pg/mL) | 19.7 | 17.4 (−12%) | 0.17 | 15.0 (−24%) | 0.16 |
| RANTES (pg/mL) | 147.1 | 832.5 (+466%) | <0.05 | 156.4 (+6%) | 0.61 |
| Interferon-g (pg/mL) | 340.0 | 296.0 (−13%) | 0.32 | 287.0 (−16%) | 0.45 |
| TNF-α (pg/mL) | 50.3 | 45.6 (−9%) | 0.46 | 20.6 (−59%) | <0.01 |
| Antithrombin (% activity) | 105.0 | 92.5 | 0.10 | 26.0 | <0.01 |
| | | 1 g beads/1 mL blood | | | |
| VCAM (ng/mL) | 115.5 | 99.5 (−14%) | 0.30 | 89.2 (−23%) | <0.05 |
| IL-6 (pg/mL) | 19.7 | 17.5 (−11%) | 0.17 | 15.9 (−19%) | 0.16 |
| RANTES (pg/mL) | 147.1 | 833.0 (+466%) | <0.05 | 156.8 (+7%) | 0.61 |
| Interferon-g (pg/mL) | 340.0 | 296.7 (−13%) | 0.32 | 287.5 (−15%) | 0.45 |
| TNF-α (pg/mL) | 50.3 | 46.3 (−8%) | 0.46 | 21.1 (−58%) | <0.01 |
| Antithrombin (% activity) | 105.0 | 93.0 | 0.10 | 26.8 | <0.01 |

Cytokine Binding

Pre- and post-column concentrations of analyzed cytokines are shown in Table 2. Briefly, passage through the heparinized beads resulted in a significantly bigger decrease in blood VCAM and TNF as compared to non-heparinized beads.

Impact of Bead Volume

Data obtained with a 1:1 and 1:10 blood-to-bead volume did not vary significantly (Table 2).

Impact of Flow Rate

Varying the blood flow rate from 1 up to 10 mL/min did not significantly affect the amount removed of the respective cytokines, indicating that the observed binding to the immobilized heparin molecules is a very rapid event and is clearly not dependent on diffusion kinetics.

Example 4

5 liters of porcine platelet poor plasma was spiked with 83 μg/L of TNF-α and recirculated at 37° C. and 150 ml/min using a conventional dialysis blood pump. 80% of the TNF-α was captured in 80 minutes.

In this example, 5 liters of platelet poor plasma in which recombinant TNF-α had been added was tested with a clinically sized cartridge. A 300 ml cartridge was packed with heparinized PE beads as described in Example 1. The device was sterilized using ETO sterilization using the 16 hour cycle with a temperature of 50 degrees. The device was allowed to "gas out" for an additional 12 hours prior to the start of the study.

5.1 L of frozen, unfiltered porcine heparinized platelet poor plasma from Innovative Research was purchased, and stored in a −20 degree freezer until the day of use. 1 mg of Recombinant Human Tumor Necrosis Factor-α was received from Invitrogen in powder form.

The morning of the procedure the plasma was removed from the −20 degree C. freezer and placed into a warm water bath to thaw. 1 ml sterile water was mixed with the 1 mg powdered TNF-α to reconstitute to a concentration of 1 mg/ml.

A Fresenius 2008K dialysis machine was set up with a "Combiset" hemodyalisis blood tubing (standard tubing used on the Fresenius machine) in a closed system set up with the seraph hemofilter in place of the Fresenius Kidney. 5 L of plasma was transferred into a 5 L reservoir bag which was connected to the arterial and venous patient lines. The dialysis machine along with tubing was primed with saline to ensure proper function and that there was no air through the closed circuit.

The 5 L bag of plasma was placed on a plate rocker with a Bair Hugger warming blanket wrapped around to maintain temperature throughout the procedure. At this point the pre-infusion control sample was collected and placed in liquid nitrogen for snap freezing. The sample was then moved to a sample storage box and placed on dry ice. After all connections were confirmed, 0.415 ml TNF-α was injected into the port of the reservoir bag. The plasma with TNF-α was allowed to mix on the rocker for 10 minutes before the post-infusion control sample was collected. The post-infusion sample was collected, snap frozen in liquid nitrogen, then moved to the sample box on dry ice. The dialysis system was purged of saline and the system clock was started when the plasma was passed through the closed system. The first sample was collected upstream from the filter at 5 minutes.

For the $1^{st}$ hour of the test run, samples were collected every 5 minutes from the port immediately upstream and also immediately downstream from the Hemofilter. The samples were snap frozen in liquid nitrogen and placed in the sample storage box on dry ice.

For the $2^{nd}$ and $3^{rd}$ hour of the test run the samples were collected every 10 minutes from the port immediately upstream and immediately downstream from the hemofilter. The samples were snap frozen in liquid nitrogen and placed in the sample storage box on dry ice.

For the $4^{th}$ and $5^{th}$ hour of the test run, samples were collected every 20 minutes from both the upstream and downstream ports. These samples were also snap frozen in liquid nitrogen, and placed in the sample storage box on dry ice.

At each sample collection, both upstream and downstream for each time point, a new needle and a new syringe was used to avoid residual TNF-α.

ELISAs were performed to monitor the amount of TNF-α in the plasma. To coat the 96-well plates, 10 μL of the capture antibody was diluted in 10 μL of coating buffer A and 100 μL was added to each well. The plate was covered with parafilm and stored at 4° C. overnight or over the weekend. Samples were removed from the −80° C. freezer, logged, and allowed to thaw. Plates were removed from the 4° C. refrigerator and wells aspirated, washed once with 400 μL/well of Assay buffer, then inverted and blotted on absorbent paper towels. 300 μL of Assay buffer were added to each well and the plates were incubated for 60 minutes. During this time, standards were prepared from the TNF-α standard included with the CytoSet by dilution in Assay buffer. Thawed samples were diluted in assay buffer. Once samples were diluted, they were replaced in the proper places in the freezer boxes and returned to the −80° C. freezer, as indicated by the log. Plates were washed again with 400 μL/well of Assay buffer, inverted, and blotted. The 100 was placed in the wells according to the ELISA template sheets. Samples and standards were run in duplicate and a standard curve was included on each plate. 8.8 μL of detection antibody was diluted in 5.49 mL Assay buffer and 50 μL was added to each well as soon as all samples and standards were added. Plates were incubated for 2 hours at room temperature on an orbital shaker. Plates were washed and aspirated 5 times as described above. The streptavidin conjugate (16 μL) was diluted in 10 mL of Assay buffer and 100 mL was added to each well. Plates were incubated 30 minutes at room temperature on the orbital shaker then washed with Assay buffer 5 times as described above. 100 μL of the TMB solution was added to each well and plates were incubated a further 30 minutes on the orbital shaker. 100 μL of the stop solution was added to each well and the plate was read at 450 nm on a Vmax plate reader within 30 minutes of adding the stop solution.

Figure 5:
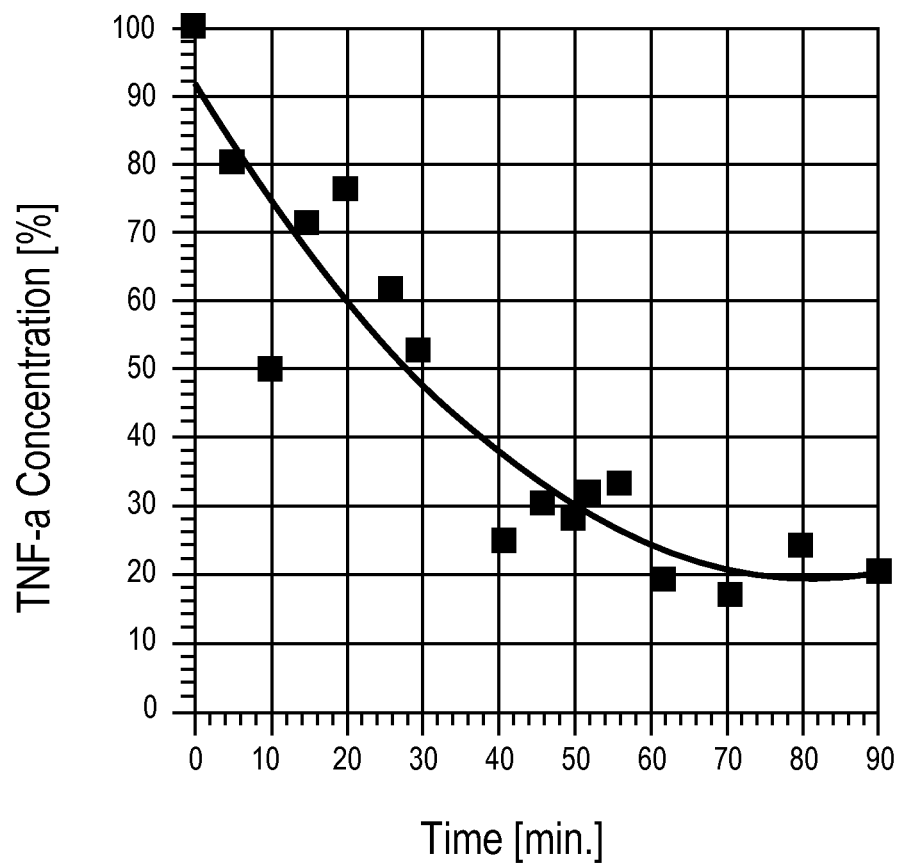
FIG. 5—Removal of TNF-α from 5 Liters of plasma using heparinized beads. Initial concentration of TNF-α was 83 μg/L.

The results of the test are plotted in FIG. 5. Within 40 minutes of continuous cycling of TNF rich serum, an 80% reduction of TNF was observed, with no subsequent release. With ideal mixing, all of the TNF in the plasma would have passed over the adsorption column in 33 minutes. Removal of TNF-α through adsorption based on convection kinetics is demonstrated as the majority of TNF was captured in this time period.

Example 5

A quartz crystal microbalance (QCM) experiment was performed to attempt to normalize the uncompetitive binding capacity of TNF-α to a heparinized surface. QCM is a technique that can detect the weight of adsorbents on specially prepared crystals. The minimum detection limit is 0.5 ng/cm$^2$. QCM detects the resonance frequency of the crystal. As the mass of the crystal increases through adsorption, the resonance frequency changes in proportion to the gain in mass. The change in mass (Δm) is described in the following equation $$\Delta m = -C \frac{1}{n} \Delta f$$

C=17.7 ngcm$^{-2}$s$^{-1}$
n–overtone
where Δf is the change in frequency.

Figure 3A:
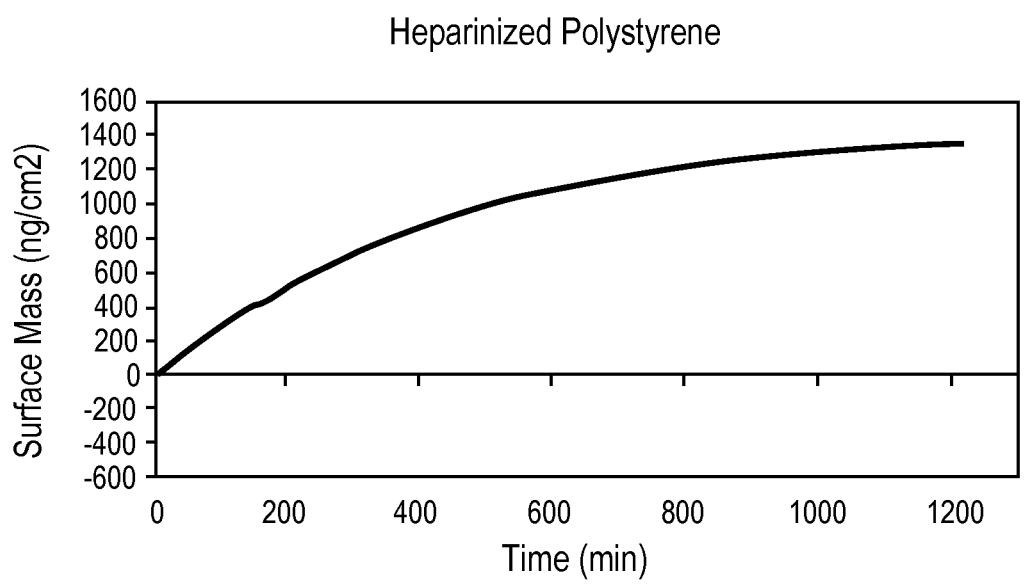
FIG. 3A—QCM plot showing specific adsorption of TNF-α on heparinized QCM crystals.
Figure 3B:
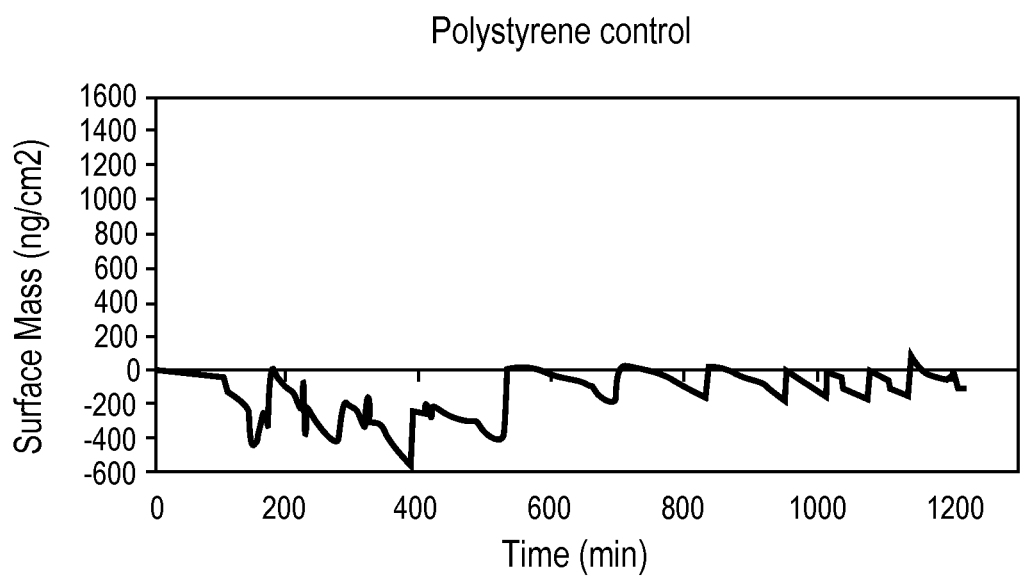
FIG. 3B—QCM plot showing no adsorption of TNF-α on control QCM crystals.

Polystyrene coated QCM crystals were heparinized following the method described in Example 1. A 120 ml solution was prepared where recombinant TNF-α was added to PBS for a final concentration of 83 μg/L. The solution was then flowed through a cell containing 4 QCM crystals at a rate of 50 μl/min. Two crystals were heparinized and two were control crystals (untreated polystyrene). The total time of the experiment was 20 hours. The results for the amount of TNF-α adsorbed on the heparinized crystals and the controls are shown in FIGS. 3A and 3B. A maximum of 1234 ng/cm$^2$ of TNF-α adsorbed on the heparinized crystal and a adsorption on the control surfaces was negligible.

Example 6

A study was performed testing the removal of cytokines from plasma sampled from *Bacillus anthracis* infected macaques using heparinized beads. The plasma was collected at the time of death of several animals and pooled. 1 ml filter syringes were packed with either 0.5 grams of PE beads heparinized following the procedure outlined in Example 1 or untreated PE beads for use as controls. A total of three sample syringes and three control syringes were used. A top porous plate was placed on top of the beads to keep the beads from floating as saline or plasma was added to the filter syringes. The filter syringes were primed using 2 ml of Tris-buffered Saline (TBS). The 2 ml of saline was passed through the filter syringe using a 5 ml syringe. The plunger of the 5 ml syringe was then retracted and filled with 4 ml of air. The air was then passed through the filter syringe to force the remaining saline out of the beads. 0.5 ml of plasma was then pulled into the 5 ml syringe and then pressed through the filter syringe. An additional 4 ml of air was passed through the filter syringe to remove any residual plasma. After the plasma drained through the syringe, aliquots were sampled and flash froze for cytokine concentration analysis. A Luminex® Multiplex assay was used to test for GRO-α, IL-8, MIP-1β, Rantes, and TNF-β. The results are summarized in Table 3.

TABLE 3

| Cytokine | Before Passage Levels (pg/ml) | Passage Through Control Beads (pg/ml) | % Removed Control | Passage Through Heparin Beads (pg/ml) | % Removed Heparin Beads |
|---|---|---|---|---|---|
| GRO-α | 263.5 | 158.5 | 39.8% | 77.66 | 70.6% |
| IL-8 | 504.9 | 460.8 | 8.7% | 312.4 | 38.1% |
| MIP-1β | 66.2 | 56.4 | 14.8% | 51.8 | 21.8% |
| RANTES | 1105.3 | 930.3 | 15.8% | 559.7 | 49.4% |
| TNF-β | 7.3 | 7.9 | −8.2% | 4.3 | 41.4% |

Example 7

Cartridge to Bind Cytokines and Endotoxins Using a Layered Assembly

A cartridge is built using two different adsorption media. Heparinized beads are used to capture cytokines and PEI beads are used to capture endotoxins. By controlling the ratio of heparinized to PEI beads, blood compatibility can be maintained. The PEI beads are made following the first two steps in Example 1.

In this example, a cartridge is built with heparinized beads and polyethyleneimine (PEI) coated beads. A 300 ml adsorption column is fixed to a vertical stand. 50 ml of 300 micron average heparinized beads are then added to the cartridge and allowed to settle. A 50:50 mixture of PEI and heparinized beads is then added and makes up the next 200 ml. The cartridge is then filled to the top with a final 50 ml of heparinized beads. The cartridge is then sealed and the close packing of the beads maintain the layered structure of the adsorption media. In this cartridge, ⅔$^{rds}$ of the beads are heparinized while ⅓$^{rd}$ is aminated and therefore inherently thrombogenic.

An in vitro experiment was then performed where a unit of human blood (500 ml) was incubated with LPS. Three different concentrations of LPS in blood were tested: 25 EU/ml, 125 EU/ml, and 250 EU/ml. Attached FIG. 10 shows the results after the three different samples of blood were re-circulated at 150 ml/min through different cartridges. The units of blood with LPS concentrations of 25 and 125 EU/ml samples showed removal of LPS to background levels after 1 hour of filtration. The unit of blood with 250 EU/ml showed a reduction of 50% after 1 hour and 65% after 2 hours. The results show that the addition of PEI modified beads increases the binding capability of the cartridge to remove LPS, which does not bind to heparin.

Example 8

Cartridge to Bind Cytokines and Endotoxins Using a Uniform Mixture of Beads

A cartridge is built using two different adsorption media. Heparinized beads are used to capture cytokines and PEI beads are used to capture endotoxins. By controlling the ratio of heparinized to PEI beads, the overall blood compatibility of the device can be maintained.

In this example, a cartridge is built with heparinized beads and PEI coated beads. A 300 ml adsorption column is fixed to a vertical stand. 100 ml of PEI coated beads are added to 200 ml of heparinized beads and mixed thoroughly. The 300 ml of beads are then added to the cartridge and sealed. The close packing of the beads maintains the random mixture of beads. In this cartridge, ⅔$^{rds}$ of the beads are heparinized while ⅓$^{rd}$ are aminated.

Example 9

Cartridge to Bind Cytokines, Gram Negative Bacteria, and Endotoxins Using a Layered Assembly A cartridge is built using three different adsorption media. Heparinized beads are used to capture cytokines, mannose functionalized beads are used to capture gram negative bacteria, and PEI beads are used to capture endotoxins. By controlling the ratio of heparinized beads, mannose functionalized beads, and PEI coated beads, blood compatibility can be maintained.

A 300 ml adsorption column is fixed to a vertical stand. 50 ml of 300 micron average heparinized beads are then added to the cartridge and allowed to settle. 200 ml of beads, with equal quantities of heparinized beads, PEI beads, and mannose functionalized beads are then added to the cartridge. The cartridge is then filled to the top with a final 50 ml of heparnized beads. The cartridge is then sealed and the close packing of the beads maintain the layered structure of the adsorption media. In this cartridge, 55.6% of the beads are heparinized, 22.2% are PEI beads, and 22.2% are mannose functionalized.

Example 10

In Vitro Removal of *B. Anthracis* PA

Bacterial Supernatants: Overnight cultures of *B. anthracis* 7702 (which produces protective antigen, PA) or 9131 (which does not produce PA) were cultured in Luria Broth (LB) at 37° C. while shaking at 250 RPM. 20 mLs of LB with 0.8% sodium bicarbonate ($NaHCO_3$) at pH 8 (pH with 1 M HEPES) was inoculated with 1 mL overnight 7702 culture and grown until late exponential phase (approximately 7 hours) while shaking at 250 RPM at 37° C. Cultures were centrifuged for 5 minutes at 3500 RPM to remove bacterial cells and debris. Supernatants were collected and passed through a 0.2 μm filter and used immediately or stored at −20° C.

Preparation of Beads: 1 g heparin or control beads were added to syringes with a filter placed in the bottom and on top of the beads. Prior to experiments, beads were prepped by the addition of 2 mLs Tris-buffered Saline (TBS). Where Fetal Bovine Serum (FBS) was used, the beads were prepped by the addition of 2 mLs TBS followed by 2 mLs FBS, which was passaged over the beads 5 times. When drops of TBS or FBS where no longer released from the syringes, bacterial supernatants were passaged.

Supernatant Passage: 2 mLs of bacterial supernatant was applied to the beads. After passage, the supernatant was collected and passaged through an additional 4 times. When drops of supernatant were no longer released from the syringes, the supernatant was collected at kept at −20° C.

ELISA: 100 μL supernatant was added to each well of an Immulon 4HBX high binding microtiter plate and incubated at room temperature for 2 hours on a rocker. The supernatant was removed and wells were washed 3 times with TBS containing 0.05% Tween (TBST). Well were blocked with 2% bovine serum albumin for 1 hour at room temperature on a rocker. Wells were washed again. Wells were incubated with goat anti-PA (List Biological Laboratories) (1:2000 dilution in TBS) for 1 hour at room temperature on a rocker. Wells were washed as described. Wells were incubated with rabbit anti-goat-HRP (Invitrogen) (1:2000 dilution in TBS) for 1 hour at room temperature on a rocker. Wells were washed as described. Wells were developed by the addition of SigmaFast-OPD (Sigma) in $dH_2O$ for approximately 30 minutes at room temperature. Absorbance was read at 450 nm.

Western Blot: Bacterial supernatants were obtained as described and 2.5 μL or 5 μL volumes were added to a PVDF membrane (BioTrace) that was prepped in methanol, followed by TBS for 3 minutes. After 5 minutes, the membrane was blocked with 2% non-fat milk in TBST for 30 minutes at room temperature. The membrane was washed 3 times with TBST and incubated with 1:3000 dilution of goat anti-PA for 45 minutes at room temperature. The membrane was washed 3 times and incubated with 1:3000 rabbit anti-goat-alkaline phosphatase for 45 minutes at room temperature. The membrane was developed with 1-step NBT/NCIP (Piercenet).

Results

It was first verified that toxin was produced under our culturing conditions using a Western/dot blot assay. Protective antigen (PA) was detected in 7702 cultures with and without atmospheric conditions of 5% $CO_2$ at 37° C. in both overnight and 8 hour cultures. FBS was used as a control for background antibody detection.

7702 and 9131 supernatants were passed through control and heparinized beads. We found approximately 75% reduction with control and heparinized beads (See FIG. 6). Compilations of replicates, to date, indicate a 43.3% reduction without pre-soak and a 75% reduction with a pre-soak after application to heparinized beads. Reduction of 75% brings the measurement of PA near background levels of 9131 indicating that there may be a 100% reduction. Reductions in PA were recovered after one passage of supernatants over the beads. Multiple passages had no effect on the reduction of PA.

Example 11

Demonstration of Cell Protection by Heparinized Beads

Figure 4:
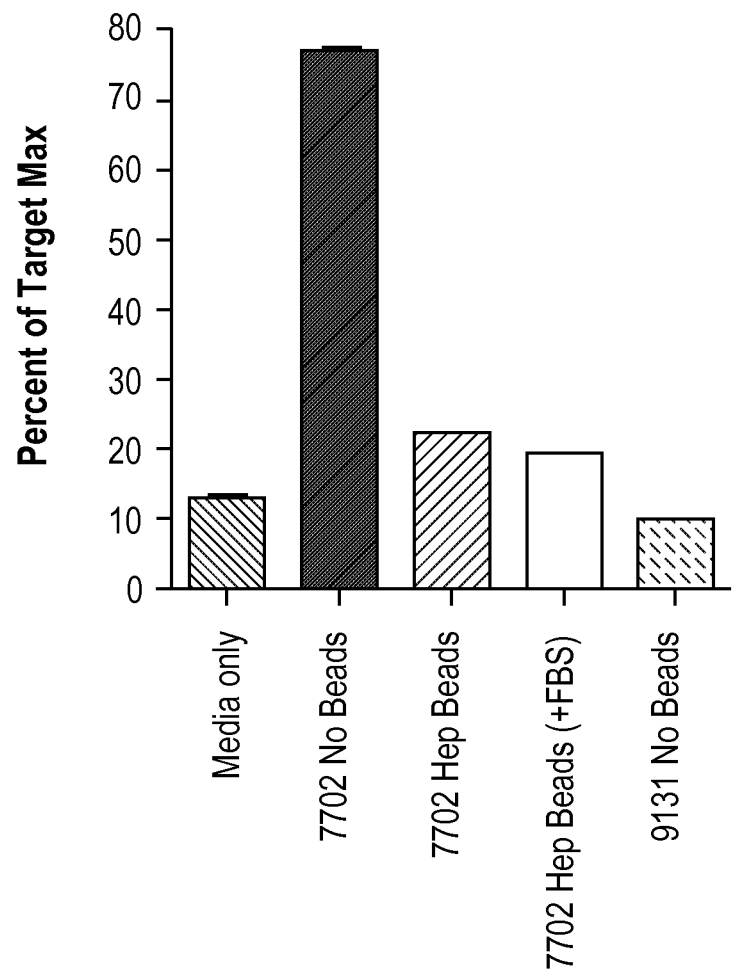
FIG. 4—Protection of macrophages from anthrax using heparinized beads. The heparinized beads captured PA before macrophages were damaged.

In this study, the same PA containing supernatants were exposed to macrophages. The level of cell death reached 80% when the heparinized beads were not used. When heparinized beads were added to the experimental setup, cell death was reduced only to 20%, indicating the capture of PA before it attacked the macrophages. PA supernatant and bead preparation were performed as outlined in example 3. Supernatents 7702 and 9131 were concentrated 7702 and 9131 to 10×. The supernatant was then diluted to desire concentration in DMEM cell culture media (-phenol red). Macrophages were cultured, counted, and resuspended to 1×10^6 cells/ml. 1×10^5 cells were added to each well in 500 μL DMEM+FBS and incubated overnight at 37 C and 5% CO2. 0.05 g beads were added to each well. DMEM+/−FBS or FBS were then passed through the transwell in 100 μl increments (total 300 μl). The media was then removed from the culture wells and the beads were washed once with DMEM. 500 μl diluted supernatants were then added to each transwell. The wells were then cultured for 20 hrs at 37 C/5% CO2. 50 ml were sampled from each transwell and LDH levels were measured (cytotoxicity). FIG. 4 shows the results. A significant reduction in Macrophage cell death was measured regardless of supernatant dilution. For beads that were treated with FBS and DMEM, cell death was reduced to background levels.

Example 12

Removal of Strain USA300 Methicilin Resistant *S. Aureaus* α-Toxin

Figure 7:
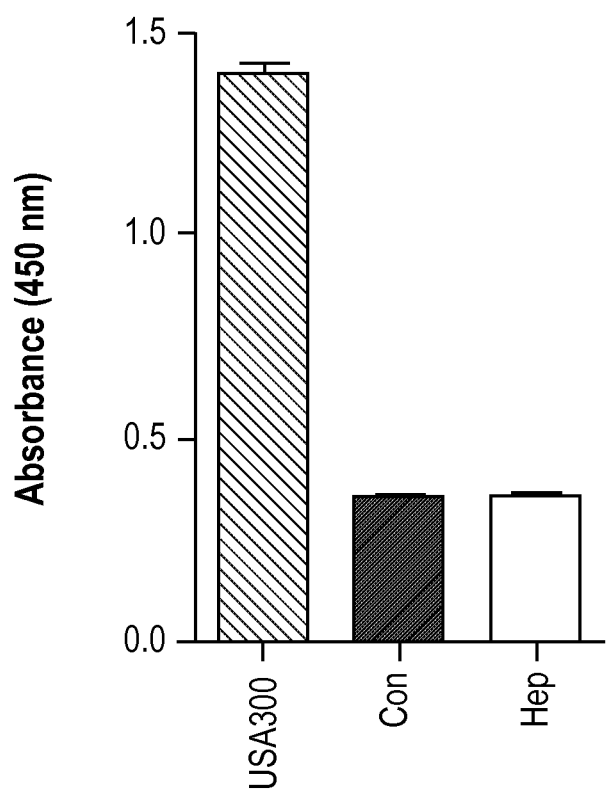

Supernatants with USA300 MRSA α-toxin were prepared using strain USA300 following the procedure outlined in Example 3. The heparinized beads were also prepared following the procedure outlined in Example 3. FIG. 7 shows the results. The concentration of α-toxin was significantly reduced regardless of supernatant dilution as measured by ELISA-type assay.

Example 13

Biocompatible High-flow Complex Fluid Manipulation

Figure 2:
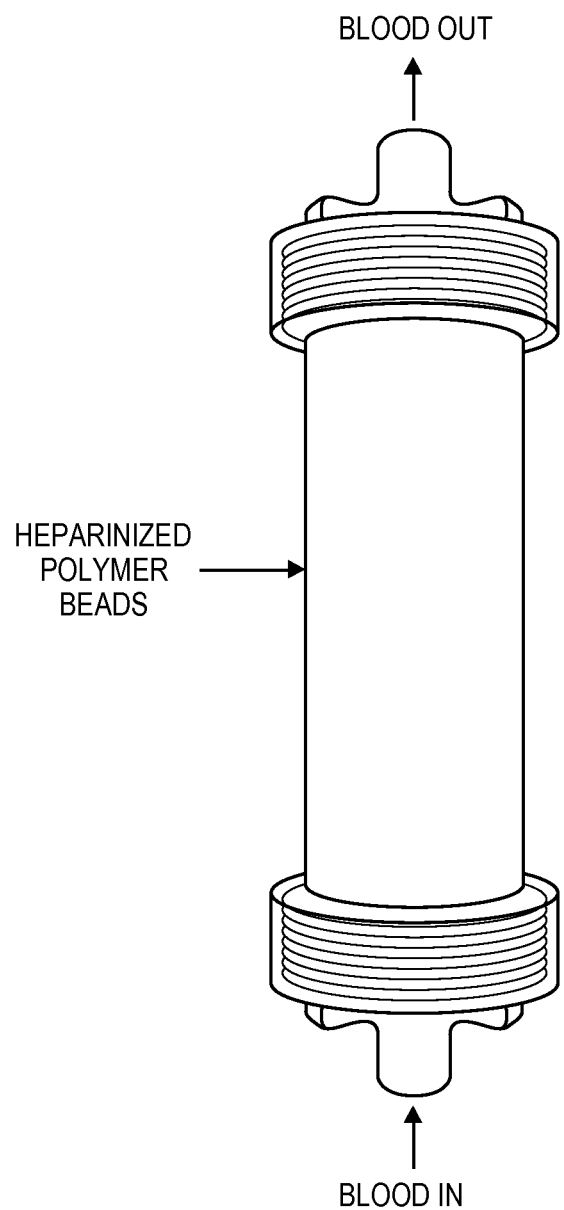
FIG. 2—picture of the column/cartridge of the present system.

Rapid adsorption rates, low-pressure-drop and laminar flow through the "tortuous micro-channels" in the present cartridge's absorption bed when it is packed with the extended broad-spectrum media are obtained with the broad-spectrum media. This has worked well with the heparin-only adsorption media and additional adsorbent sites do not appear to negatively affect these desirable properties. An example of the cartridge can be seen in FIG. 2.

Blood fractionation is not required for the blood being treated in the present DLT separation cartridge. Microchannels, which constitute a carefully-controlled fraction of the separation column's internal volume, are created within close packed adsorption media having a tight size distribution. This and the present high flow rates and rapid adsorption kinetics make the DLT system useful even in series flow with a dialyzer when necessary. It also reduces treatment time to a few hours or less without activating complement. This approach to a separation process that does not require systemic anticoagulation is effective for the bulk flow of blood being treated by the DLT.

Figure 9:
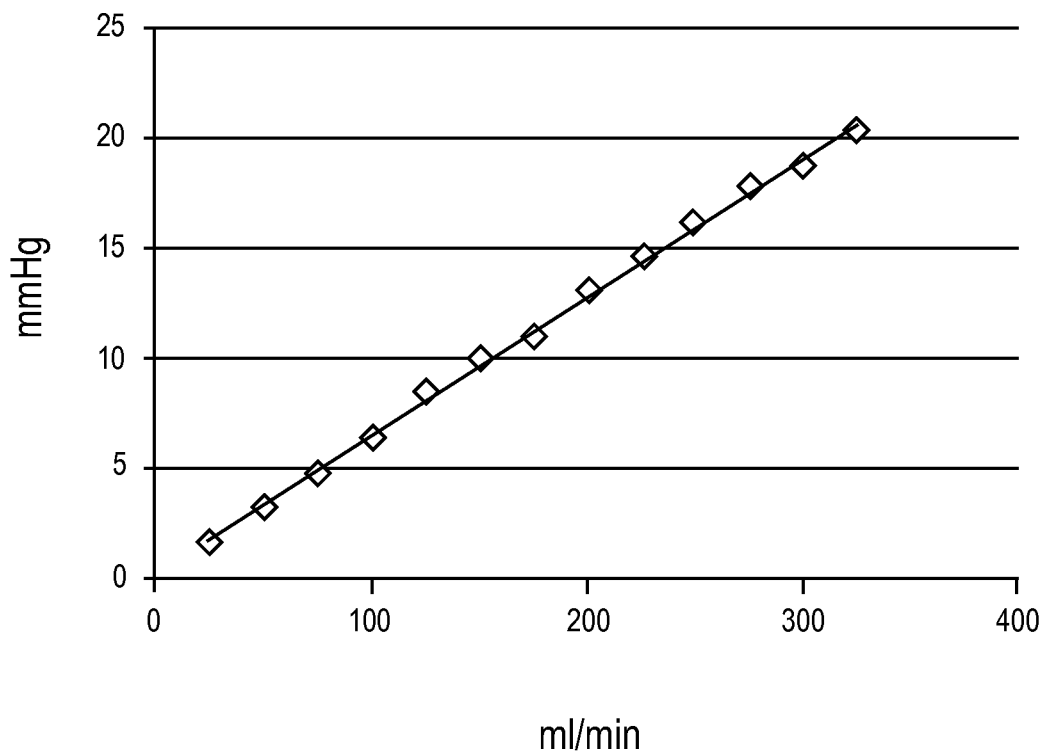

For example, the large number of micro-machined channels needed to accommodate as least 1200 mL/hr (at shear rates that do not cause cell damage) suggests that this technology should be reserved for use in sensors as discussed above. It may not be practical for the much higher flow rates of the main extracorporeal circuit. With the present approach to fluid management this task becomes very straightforward. It includes testing separation cartridges with candidate adsorbent media on a mock circulation loop with a glycerin/water blood analogue. The adsorbent size/distribution and the column packing is varied, including the distribution of mixed adsorbent types within the column, to achieve pressure drops comparable to the heparin-only column: 3 mm Hg at 20 mL/min, 15 mm at 200 ml/min. If this pressure drop goal is not met the column diameter is increased to reduce pressure drop. FIG. 9 demonstrates the low pressure drop as a function of flow rate.

Example 14

Testing Broad-Spectrum Capability of the System

The present inventors have tested the broad-spectrum capability of a heparinized media. For example, in an in vitro blood study, 85% of MRSA was removed by a single pass through the media (See Table 4 below). Protective antigen (PA) produced by B. anthracia was reduced to background levels and captured before macrophages could be harmed (FIG. 4) In addition, several in vitro studies have shown significant capture of TNF-α, 11-6, GRO-α, 11-8 and RANTES without removing important proteins such as albumin and Protein-C (Table 3). To demonstrate the rapid convection kinetics of the device, 5 liters of platelet poor plasma, spiked with 83 µg/L of TNF-α was passed over a cartridge. Within 80 minutes, only 20% of the TNF-α remained (FIG. 5).

TABLE 4

Percentage of corresponding non-passed suspensions

| Bacterial Strain | | SA1800T | MRSA485 | MRSA251 | MRSA860 |
|---|---|---|---|---|---|
| Heparinized | Void | 38 | 14.8 | 41.2 | 30.4 |
| Beads | Wash | 1.2 | <3.7 | 2.3 | 9.1 |
| | Elute | 23 | 50 | 8.8 | 11.1 |
| Control | Void | 57 | ND | 37.7 | 41.3 |
| hydrophilic | Wash | <1.2 | ND | 3.3 | 3 |
| beads | Elute | 1.4 | ND | 0.35 | 0.18 |
| Viable Bacteria added | | $7.5 \times 10^5$ | $4 \times 10^5$ | $3.4 \times 10^5$ | $4.6 \times 10^5$ |

Although heparin can bind many pathogens, inflammatory molecules, and coagulation factors, it cannot remove all of the targeted blood-borne factors. For instance, endotoxins are negatively charged, and will not bind to the negatively charged heparin surface.

Medical has identified surface chemistries that can bind many additional pathogens, but several candidate surfaces are inherently thrombogenic. However, by optimally mixing heparinized adsorption media with new surface chemistries, at the nano- or micro-scale, it is possible maintain the overall anti-thrombogenic properties of the heparin-only cartridge, so systemic anti-coagulation is optional.

Initial directionality toward risk and tolerance of false positives and false negatives is established for future biostatistical modeling.

Blood-borne factors of interest are initially tested in vitro to determine their affinity for heparin-only media. In parallel, new surface chemistries are developed to present either sialic acid functionalized, mannose functionalized, a positively charged surface, and/or an antimicrobial surface. Physical mixtures of the heparin-only media, and the new media are tested in combination to optimize pathogen capture while maintaining anti-thrombogenecity. This process is iterative. After demonstration of broad spectrum capture, the surface area is optimized to yield increased capture yield.
Removal of Bacterial Pathogens In addition, due to its very broad-spectrum binding capability, this separation cartridge is also an effective countermeasure against bio-agents such as anthrax. Although antibiotics, such as ciprofloxacin, can kill B. anthracis in the blood, the PA toxin remains in the blood and continues to kill macrophages, leading to extreme inflammation. During the anthrax attack of 2001 in Washington D.C., five of the 11 victims who contracted inhalational anthrax died. A low cost DLT, with the capability of removing PA and inflammatory molecules could be an effective device against a weaponized anthrax attack.

Bacterial biothreat agents (anthrax ames, plague and tularemia Schu 4) are used to inoculate guinea pigs. Infection with these agents results in a fatal disease characterized by bacteremia leading to bacterial dissemination. Animals are treated with the rodent device post challenge. Blood is collected for bacterial load determination just prior to and after treatment.

Example 15

Large Animal Testing

A baboon model is selected for the study. Initial investigation has found that the circuit volume acceptable for an adult human may be slightly too large for a baboon study, therefore a smaller void volume separation column may need to be used depending on the input from veterinarians. The large animals are optionally tethered to allow for a DLT therapy since an animal cannot remain under general anesthesia for the length of the DLT procedure.

The filter cartridge of the invention is based on surface-immobilized, 'end-point-attached' heparin on a high surface-area adsorbent, packed into a cylindrical cartridge between porous filter plates. Heparin, a widely-used, FDA approved anticoagulant is also known for its anti-inflammatory and anti-microbial properties. The device creates a diversion for harmful substances in the blood. Instead of targeting cells, harmful agents are attracted to the surface-bound heparin within the cartridge, and removed from circulation when the cartridge is removed from the extracorporeal circuit. The immobilized heparin does not enter the blood stream, yet it is responsible for both the anti-thrombogenic safety and binding efficacy of the treatment method. Several experiments have demonstrated the broad-spectrum potential of the technology. In these experiments, human scale prototypes or miniature cartridges have been used to investigate capture of harmful agents from blood, plasma, or sera.

Results: The results of these experiments include the following:

Removal of TNF-α (59%) and IL-6 (25%) from human septic blood

High TNF-α Binding Capacity vitro porcine serum recirculation study removed 80% of TNF-α in 80 minutes X MRSA bacteria removed from blood in high yield Anthrax Protective Antigen captured by the media Cytokines removed from anthrax-infected macaque blood Macrophage cells protected from Anthrax Protective Antigen toxin These experiments have shown the device to be effective as an inherently anti-thrombogenic, broad-spectrum blood 'filter' to remove inflammatory molecules, pathogens, and toxins from sepsis patients.

The device system of the invention is 1) broad spectrum in removing harmful agents from blood, 2) relies on fast kinetics, 3) present a surface that is anti-thrombogenic and anti-inflammatory, 4) operates with a low pumping pressure and 5) can be easily scalable for low cost and mass deployment.

Heparin is very similar in chemistry to heparan sulfate (HS), a polysaccharide found within syndecans on cell surfaces. The HS segments on syndecans, as co-receptors for many molecules and pathogens, modulate many biological processes and are capable of binding proteins, toxins, and pathogens. The high-surface-area heparinized cartridge bed useful in the invention creates a diversion for harmful substances in the blood. Instead of binding to HS segments on endothelial cells in vivo, these molecules are diverted to the surface-bound heparin within the cartridge, and removed from circulation when the cartridge is removed from the extra-corporeal circuit.

Combining this technology of immobilized heparin media with conventional fluid management and pumping technologies, and advanced molecular biology detection methods using point of care sensor arrays, the invention can provide a portable sepsis detection and treatment system for use in the field.

We claim:

1. A system for broad-spectrum whole-blood extracorporeal separation of blood-borne factors of interest comprising:
    an extracorporeal solid substrate or cartridge, wherein the solid substrate or cartridge is a broad-spectrum, anti-thrombogenic cartridge having a solid substrate, which is essentially nonporous, comprising covalently-bonded, end-point attached heparin on a high-surface-area polymer substrate;
    one or more biosensors, wherein the one or more biosensors is an extracorporeal sensor for a nitric oxide biomarker; and
    an extracorporeal pump for the extracorporeal circulation of blood, and a patient monitor, wherein the system extracorporeally separates blood-borne factors of interest from whole blood.

2. The system of claim 1 wherein the extracorporeal solid substrate is disposable.

3. The system of claim 1 further comprises at least one additional extracorporeal sensor selected from the group consisting of a blood pressure sensor, a temperature sensor, a pressure sensor, a blood glucose sensor, a blood gas sensor, or a sensor which detects nitric oxide (NO) metabolites, a sensor that detects cytokines, a sensor that detected bacteria or bacteria toxins, a sensor that detects viruses, a sensor that detects parasites, a sensor that detects fungi, a sensor that detects coagulation factors, a sensor that detects organ dysfunction proteins, a sensor that detects acute phase proteins, or a sensor that detects complement factors.

4. The system of claim 3, wherein the at least one additional extracorporeal sensor quantifies the amount of an additional biomarker in blood.

5. The system of claim 3, wherein the at least one additional extracorporeal sensor measures pressure readings, biosensor outputs, patient temperature, blood gas, or blood pressure.

6. The system of claim 5, comprising alarms correlated to cartridge pressure drop, biosensor output, patient data or system data.

7. The system of claim 1, wherein the one or more biosensors amperometrically detects blood-borne factors.

8. The system of claim 1, wherein the one or more biosensors chemometrically analyzes the presence and amount of blood-borne factors.

9. The system of claim 1, wherein the extracorporeal pump is a roller pump.

10. The system of claim 1 further comprising a extracorporeal power source.

11. An extracorporeal method for broad-spectrum whole-blood separation of blood-borne factors of a patient, comprising:
    (a) detecting the presence or amount of a blood-borne factor of interest using an extracorporeal biosensor,
    (b) bringing a sample of blood in contact using convection transport with a broad-spectrum, anti-thrombogenic extracorporeal cartridge having a solid substrate, which is essentially nonporous, comprising covalently-bonded, end-point attached heparin on a high-surface-area polymer substrate, and
    (c) separating the sample from said broad-spectrum, anti-thrombogenic cartridge whereby said blood-borne factor is at least partially retained on said extracorporeal cartridge and the removed sample has a reduced amount of blood-borne factor.

12. The method of claim 11, wherein the extracorporeal biosensor detects an elevation in a biomarker.

13. The method of claim 11, wherein the extracorporeal biosensor detects levels of biomarkers in a patient at two or more time points.

14. The method of claim 11, wherein the extracorporeal biosensor continuously detects levels of biomarkers.

15. The method of claim 11, wherein the method further includes measuring a blood pressure of the patient using a blood pressure sensor.

16. The method of claim 11, where the blood-borne factors are separated without the prior identification of specific pathogens.

17. The method of claim 11, further comprising measuring pressure drop over the extracorporeal cartridge, extracorporeal biosensor output, or patient data.

18. The method of claim 17, further comprising alarming for caregiver feedback based on biosensor's output.

19. The method of claim 17, wherein the method further comprising telemetry of measurements of patient data.

20. The method of claim 11, further comprising data logging, trending, and alarming for caregiver feedback, based on biosensor output.

* * * * *